US007758203B2

(12) United States Patent
McMahon et al.

(10) Patent No.: US 7,758,203 B2
(45) Date of Patent: Jul. 20, 2010

(54) POWER CONNECTIONS AND INTERFACE FOR COMPACT ILLUMINATOR ASSEMBLY

(75) Inventors: Michael T. McMahon, Syracuse, NY (US); Steven R. Slawson, Camillus, NY (US); Dale C. Saddlemire, Cortland, NY (US)

(73) Assignee: Welch Allyn, Inc., Skaneateles Falls, NY (US)

( * ) Notice: Subject to any disclaimer, the term of this patent is extended or adjusted under 35 U.S.C. 154(b) by 0 days.

(21) Appl. No.: 11/731,189

(22) Filed: Mar. 30, 2007

(65) Prior Publication Data

US 2007/0230167 A1 Oct. 4, 2007

Related U.S. Application Data

(60) Provisional application No. 60/876,346, filed on Dec. 21, 2006.

(51) Int. Cl.
*F21L 4/00* (2006.01)
*A61B 1/00* (2006.01)
*F21S 4/00* (2006.01)

(52) U.S. Cl. ........................ 362/183; 362/572; 362/200

(58) Field of Classification Search ................. 362/183, 362/190, 191, 647, 652, 655–659, 208, 253, 362/85, 86, 88, 119, 200, 572, 573, 574; 320/114, 115, 107, 111; 439/224, 217, 218
See application file for complete search history.

(56) References Cited

U.S. PATENT DOCUMENTS

| | | | |
|---|---|---|---|
| 3,934,578 | A | 1/1976 | Heine |
| 3,945,371 | A | 3/1976 | Adelman |
| 3,978,850 | A | 9/1976 | Moore et al. |
| 245,515 | A | 8/1977 | Troutner et al. |
| 4,067,323 | A | 1/1978 | Troutner et al. |
| 4,156,424 | A | 5/1979 | Burgin |
| 4,263,899 | A | 4/1981 | Burgin |
| 4,337,763 | A | 7/1982 | Petrassevich |
| 4,432,351 | A | 2/1984 | Hoary |
| 4,502,468 | A | 3/1985 | Burgin |
| 4,546,761 | A | 10/1985 | McCullough |
| 4,562,832 | A | 1/1986 | Wilder et al. |
| 4,566,439 | A | 1/1986 | Burgin |
| 4,597,383 | A | 7/1986 | VanDerBel |
| 4,607,623 | A | 8/1986 | Bauman |
| 4,619,248 | A | 10/1986 | Walsh |

(Continued)

FOREIGN PATENT DOCUMENTS

JP 10078068 A * 3/1998

(Continued)

OTHER PUBLICATIONS

International Search Report/Written Opinion (ISR/WO), Jun. 5, 2008. 8 pages.

(Continued)

*Primary Examiner*—Jong-Suk (James) Lee
*Assistant Examiner*—David R Crowe

(57) ABSTRACT

A portable illuminator includes a contained power source and an integrally contained light source that is selectively inserted into the handle portion of a vaginal speculum. The portable illuminator includes an electrical interface that permits selective connection to at least two electrical devices for purposes of at least one of supplementing, replacing and recharging the contained power source.

33 Claims, 10 Drawing Sheets

U.S. PATENT DOCUMENTS

| | | | | |
|---|---|---|---|---|
| 4,638,792 | A | 1/1987 | Burgin | |
| 4,766,887 | A | 8/1988 | Cecil, Jr. et al. | |
| 299,532 | A | 1/1989 | Cecil, Jr. et al. | |
| 4,979,498 | A | 12/1990 | Oneda et al. | |
| 5,018,507 | A | 5/1991 | Montaldi | |
| 5,026,368 | A | 6/1991 | Adair | |
| 5,054,906 | A | 10/1991 | Lyons, Jr. | |
| 5,143,054 | A | 9/1992 | Adair | |
| 5,159,256 | A * | 10/1992 | Mattinger et al. | 320/115 |
| 5,165,387 | A | 11/1992 | Woodson | |
| 5,174,278 | A | 12/1992 | Babkow | |
| 5,179,937 | A | 1/1993 | Lee | |
| 5,179,938 | A | 1/1993 | Lonky | |
| 5,329,938 | A | 7/1994 | Lonky | |
| 5,374,395 | A | 12/1994 | Robinson et al. | |
| 5,394,863 | A | 3/1995 | Sanford et al. | |
| 5,465,709 | A | 11/1995 | Dickie et al. | |
| 5,475,271 | A | 12/1995 | Shibasaki et al. | |
| 5,515,303 | A | 5/1996 | Cargin, Jr. et al. | |
| 5,517,434 | A | 5/1996 | Hanson et al. | |
| 5,521,370 | A | 5/1996 | Hanson | |
| 5,552,701 | A | 9/1996 | Veteran et al. | |
| 5,588,950 | A * | 12/1996 | Sano et al. | 600/178 |
| 5,619,398 | A | 4/1997 | Harrison et al. | |
| 5,621,890 | A | 4/1997 | Notarianni et al. | |
| 5,635,814 | A | 6/1997 | Afzal et al. | |
| 5,640,004 | A | 6/1997 | Mardinian et al. | |
| 5,656,014 | A | 8/1997 | Rooney et al. | |
| 5,668,977 | A | 9/1997 | Swanstrom et al. | |
| 5,686,808 | A | 11/1997 | Lutz | |
| 5,699,226 | A | 12/1997 | Cavello | |
| 5,716,329 | A | 2/1998 | Dieter | |
| 5,746,495 | A * | 5/1998 | Klamm | 362/577 |
| 5,785,648 | A | 7/1998 | Min | |
| 5,844,472 | A | 12/1998 | Lee | |
| 5,846,249 | A | 12/1998 | Thompson | |
| 5,852,370 | A | 12/1998 | Ko | |
| 5,865,729 | A | 2/1999 | Meehan et al. | |
| 5,873,820 | A | 2/1999 | Norell | |
| 5,907,753 | A | 5/1999 | Kumar et al. | |
| 5,916,150 | A | 6/1999 | Sillman | |
| 5,916,151 | A | 6/1999 | Charters | |
| 5,955,797 | A | 9/1999 | Kim et al. | |
| 6,004,265 | A | 12/1999 | Hsu et al. | |
| 6,011,687 | A | 1/2000 | Gluskoter et al. | |
| 6,048,308 | A | 4/2000 | Strong | |
| 6,070,478 | A | 6/2000 | Krajec et al. | |
| 6,154,010 | A | 11/2000 | Geiger | |
| 6,161,938 | A * | 12/2000 | Kish et al. | 362/183 |
| 6,171,555 | B1 | 1/2001 | Cargill et al. | |
| 6,176,824 | B1 | 1/2001 | Davis | |
| 6,184,654 | B1 | 2/2001 | Bachner, III et al. | |
| 6,186,944 | B1 | 2/2001 | Tsai | |
| 6,217,512 | B1 | 4/2001 | Salo et al. | |
| 6,277,067 | B1 | 8/2001 | Blair | |
| 6,283,777 | B1 * | 9/2001 | Canova et al. | 439/218 |
| 6,285,911 | B1 | 9/2001 | Watts, Jr. et al. | |
| 6,298,738 | B1 | 10/2001 | Krajec et al. | |
| 6,319,199 | B1 | 11/2001 | Sheehan et al. | |
| 6,350,040 | B1 * | 2/2002 | Parker | 362/183 |
| 6,361,489 | B1 | 3/2002 | Tsai | |
| 6,379,296 | B1 | 4/2002 | Baggett | |
| 6,379,299 | B1 | 4/2002 | Borodulin et al. | |
| 6,394,950 | B1 | 5/2002 | Weiss | |
| 6,432,049 | B1 | 8/2002 | Banta et al. | |
| 6,436,033 | B2 | 8/2002 | Tan | |
| 6,450,952 | B1 | 9/2002 | Rioux et al. | |
| 6,487,440 | B2 | 11/2002 | Deckert et al. | |
| 6,509,715 | B1 | 1/2003 | LaRue | |
| 6,524,240 | B1 | 2/2003 | Thede | |
| 6,524,259 | B2 | 2/2003 | Baxter-Jones et al. | |

| | | | | |
|---|---|---|---|---|
| 6,535,714 | B2 | 3/2003 | Melker et al. | |
| 6,580,948 | B2 | 6/2003 | Haupert et al. | |
| 6,584,336 | B1 | 6/2003 | Ali et al. | |
| 6,589,168 | B2 | 7/2003 | Thompson | |
| 6,593,528 | B2 | 7/2003 | Franklin-Lees et al. | |
| 6,594,146 | B2 | 7/2003 | Frangesch et al. | |
| 6,595,917 | B2 | 7/2003 | Nieto | |
| 6,626,825 | B2 | 9/2003 | Tsai | |
| 6,629,525 | B2 | 10/2003 | Hill et al. | |
| 6,661,200 | B2 | 12/2003 | Odaohhara et al. | |
| 6,663,576 | B2 | 12/2003 | Gombrich et al. | |
| 6,737,830 | B2 | 5/2004 | Bean et al. | |
| 6,739,744 | B2 | 5/2004 | Williams et al. | |
| 6,756,765 | B2 | 6/2004 | Bruning | |
| 6,761,687 | B1 | 7/2004 | Doshi et al. | |
| 6,766,112 | B2 | 7/2004 | Uchiyama et al. | |
| 6,766,175 | B2 | 7/2004 | Uchiyama | |
| 6,830,547 | B2 | 12/2004 | Weiss | |
| 6,849,237 | B2 | 2/2005 | Housefield et al. | |
| 6,866,527 | B2 | 3/2005 | Potega | |
| 6,876,173 | B2 | 4/2005 | Mastaler et al. | |
| 6,920,575 | B2 | 7/2005 | Odaohhara et al. | |
| 6,923,688 | B1 | 8/2005 | Burson et al. | |
| 6,945,803 | B2 | 9/2005 | Potega | |
| 6,962,566 | B2 | 11/2005 | Quistgaard et al. | |
| 6,981,895 | B2 | 1/2006 | Potega | |
| 6,986,686 | B2 | 1/2006 | Shibata et al. | |
| 7,014,340 | B2 | 3/2006 | Bettis | |
| 7,022,075 | B2 | 4/2006 | Grunwald et al. | |
| 7,024,574 | B2 | 4/2006 | Odaohhara et al. | |
| 7,034,555 | B2 | 4/2006 | Tan et al. | |
| 7,059,769 | B1 | 6/2006 | Potega | |
| 7,072,675 | B1 | 7/2006 | Kanakubo | |
| 7,075,270 | B1 | 7/2006 | Blum | |
| 7,086,859 | B2 | 8/2006 | Gregorio et al. | |
| 7,108,437 | B2 | 9/2006 | Silverbrook et al. | |
| 7,119,835 | B2 | 10/2006 | Gennetten et al. | |
| 7,140,745 | B2 * | 11/2006 | Yuen | 362/183 |
| 2001/0002552 | A1 | 6/2001 | Vinci | |
| 2001/0029044 | A1 | 10/2001 | Gombrich et al. | |
| 2002/0001794 | A1 | 1/2002 | Melker et al. | |
| 2002/0007198 | A1 | 1/2002 | Haupert et al. | |
| 2002/0022769 | A1 | 2/2002 | Smith et al. | |
| 2002/0038075 | A1 | 3/2002 | Tsai | |
| 2002/0038076 | A1 | 3/2002 | Sheehan et al. | |
| 2002/0055670 | A1 | 5/2002 | Weiss | |
| 2002/0064041 | A1 * | 5/2002 | Parker | 362/183 |
| 2002/0071035 | A1 | 6/2002 | Sobol | |
| 2002/0072390 | A1 | 6/2002 | Uchiyama | |
| 2002/0082479 | A1 | 6/2002 | Frangesch et al. | |
| 2002/0106932 | A1 | 8/2002 | Holland et al. | |
| 2002/0134570 | A1 | 9/2002 | Franklin-Lees et al. | |
| 2002/0156350 | A1 | 10/2002 | Nieto | |
| 2002/0158605 | A1 * | 10/2002 | Sharrah et al. | 320/115 |
| 2002/0165435 | A1 | 11/2002 | Weiss | |
| 2002/0170823 | A1 | 11/2002 | Housefield et al. | |
| 2002/0175654 | A1 * | 11/2002 | Takano et al. | 320/115 |
| 2002/0177373 | A1 | 11/2002 | Shibata et al. | |
| 2002/0198471 | A1 | 12/2002 | Baxter-Jones et al. | |
| 2003/0009102 | A1 | 1/2003 | Quistgaard et al. | |
| 2003/0013959 | A1 | 1/2003 | Grunwald et al. | |
| 2003/0139673 | A1 | 7/2003 | Vivenzio et al. | |
| 2003/0158502 | A1 | 8/2003 | Baxter-Jones et al. | |
| 2003/0176772 | A1 | 9/2003 | Yang | |
| 2003/0186592 | A1 | 10/2003 | Potega | |
| 2003/0187331 | A1 | 10/2003 | Faludi et al. | |
| 2003/0197679 | A1 | 10/2003 | Ali et al. | |
| 2003/0207603 | A1 | 11/2003 | Potega | |
| 2004/0009702 | A1 | 1/2004 | Potega | |
| 2004/0026829 | A1 | 2/2004 | Van Der Weegen | |
| 2004/0052679 | A1 | 3/2004 | Root et al. | |
| 2004/0138569 | A1 | 7/2004 | Grunwald et al. | |
| 2004/0141175 | A1 | 7/2004 | Baldwin et al. | |

| | | | | |
|---|---|---|---|---|
| 2004/0183482 | A1 | 9/2004 | Roberts et al. | |
| 2004/0184288 | A1 * | 9/2004 | Bettis | 362/572 |
| 2004/0186355 | A1 | 9/2004 | Stong et al. | |
| 2004/0201680 | A1 | 10/2004 | Gennetten et al. | |
| 2004/0225310 | A1 | 11/2004 | Culp et al. | |
| 2004/0253563 | A1 | 12/2004 | Gregorio et al. | |
| 2005/0020892 | A1 | 1/2005 | Acosta et al. | |
| 2005/0065417 | A1 | 3/2005 | Ali et al. | |
| 2005/0117951 | A1 | 6/2005 | Silverbrook | |
| 2005/0162848 | A1 * | 7/2005 | Dalton et al. | 362/157 |
| 2005/0265035 | A1 * | 12/2005 | Brass et al. | 362/451 |
| 2005/0280393 | A1 * | 12/2005 | Feldmann | 320/114 |
| 2006/0001920 | A1 | 1/2006 | Moreno et al. | |
| 2006/0052144 | A1 | 3/2006 | Seil et al. | |
| 2006/0066753 | A1 | 3/2006 | Gennetten et al. | |
| 2006/0074558 | A1 | 4/2006 | Williamson et al. | |
| 2006/0087286 | A1 | 4/2006 | Phillips et al. | |
| 2006/0120069 | A1 | 6/2006 | West | |
| 2008/0043459 | A1 * | 2/2008 | Canino et al. | 362/119 |

FOREIGN PATENT DOCUMENTS

| | | | |
|---|---|---|---|
| WO | WO 2006/107877 | A2 | 10/2006 |
| WO | WO 2006/121530 | A2 | 11/2006 |

OTHER PUBLICATIONS

International Search Report/Written Opinion (ISR/WO), Jun. 5, 2008. 7 pages.

* cited by examiner

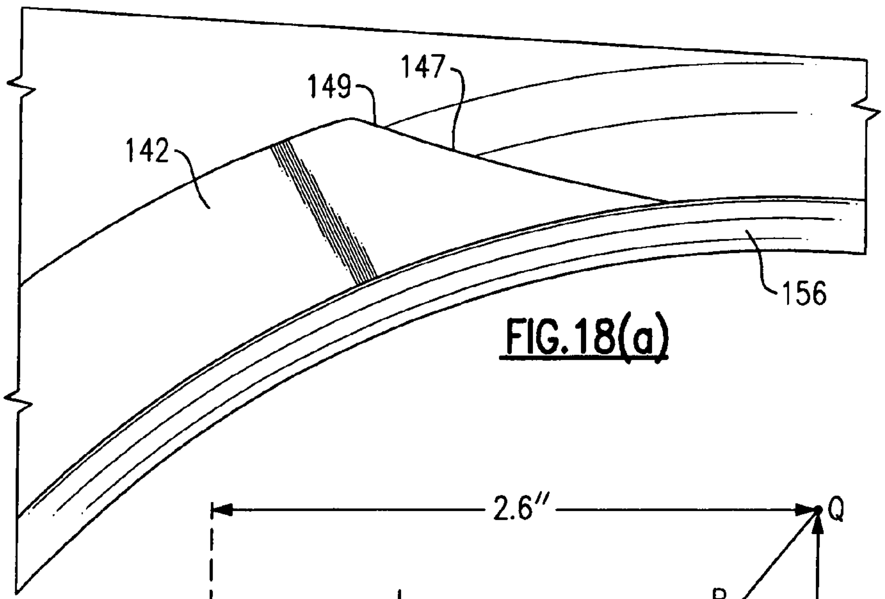
FIG.18(a)
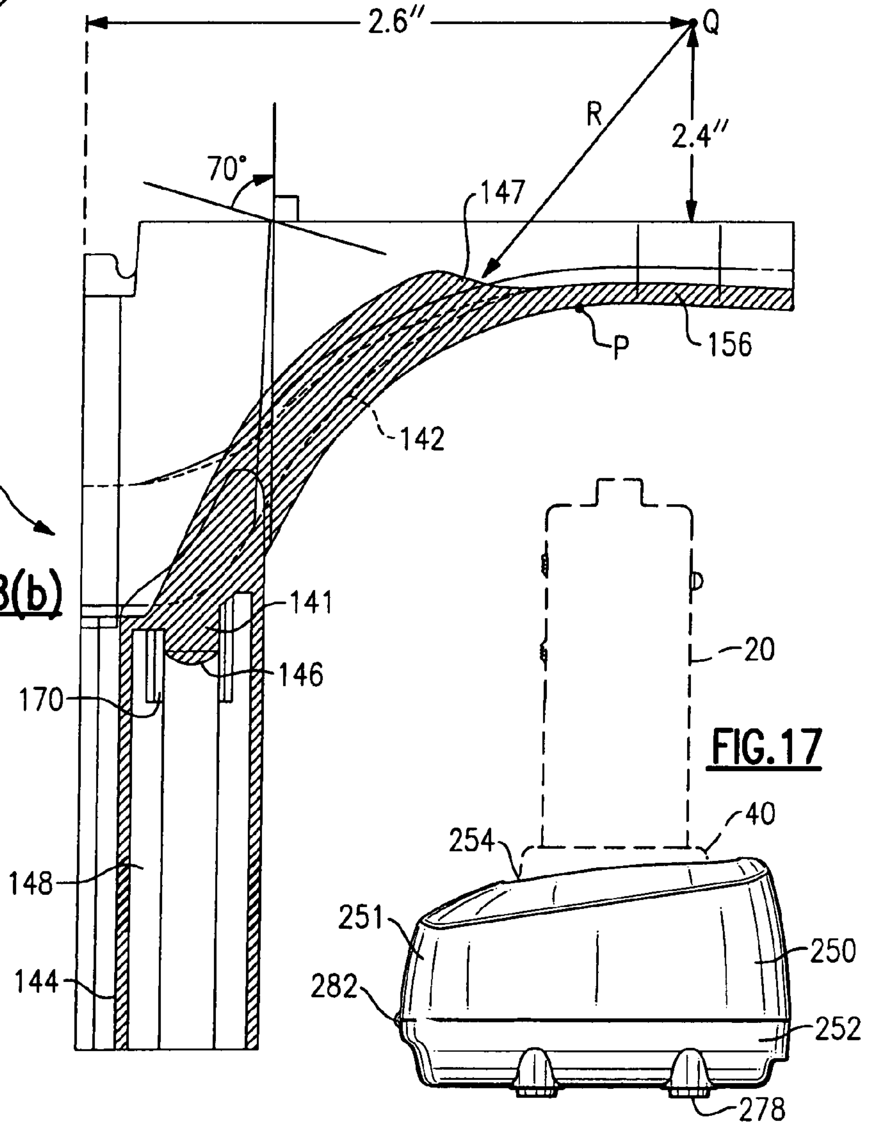
FIG.18(b)
FIG.17

POWER CONNECTIONS AND INTERFACE FOR COMPACT ILLUMINATOR ASSEMBLY

CROSS REFERENCE TO RELATED APPLICATIONS

This application is a nonprovisional application filed under 35 U.S.C. §119 and based upon U.S. Ser. No. 60/876,346, filed Dec. 21, 2006. This application is also a continuation in part (CIP) application filed under 35 U.S.C. §120 of PCT PCT/US2006/12116, filed Apr. 3, 2006, PCT/US 2006/12320, filed Apr. 3, 2006, and PCT/US2006/012322, filed Apr. 3, 2006. This application also further relates to commonly assigned and concurrently filed U.S. Ser. No. 11/731,631, the entire contents of each of the preceding documents being incorporated by reference herein.

FIELD OF THE INVENTION

The invention relates to the field of diagnostic medical devices and in particular to a portable illuminator containing a primary power source. The portable illuminator has an interface that enables use with at least two different electrical devices in order to recharge, supplement and/or replace the contained primary power source.

BACKGROUND OF THE INVENTION

Presently, vaginal specula are used in the diagnostic medical field to examine the cervix of a female patient. A number of various specula have been developed, including disposable plastic versions that are designed for single use or single patient use. Applicant has previously developed a line of disposable plastic vaginal specula that are defined by an upper blade and a lower blade, the latter including a pistol-grip like handle portion having a receiving cavity that is sized to retain an illumination assembly. The handle portion further includes a curved light pipe disposed in the upper end of the handle portion and along the lower blade wherein light from the illumination assembly is directed towards the target. The illumination assembly includes a housing containing a miniature light source, such as a miniature incandescent lamp, which is tethered by means of a cable to a power source, such as a wall transformer. The user grips the handle portion having the inserted illumination assembly and views the cervix after the blades have been opened in the patient through articulation of the blades. The cervix is viewed through an aperture formed in the proximal end of the speculum. The speculum is discarded after use, but the illumination assembly is reusable between patients.

A number of problems have been discovered in the use and maintenance of such apparatus. For example, the use of a tethered illumination assembly that requires an AC or similar power source is often inconvenient in the field, particularly remote areas in which access to such a power supply is uncertain. In addition, the use of a tethered illumination assembly presents access and other issues, for example, with bed-ridden patients. There are similar concerns relating to the use of incandescent lamps as a light source in that such sources are typically sealed within the housing of the illumination assembly and are subject to breakage, for example, if the illumination assembly is dropped. Incandescent lamps produce significant heat, which is a concern to both the caregiver and the patient, and have a finite service life, requiring periodic teardown or replacement of the entire illumination assembly. In addition, incandescent lamps are relatively expensive, as compared, for example, with other types of commercially available light sources, thereby impacting the cost of such apparatus.

Though there is a desired need to be able to provide a portable power source to permit versatility in patient examinations, this need has been further frustrated with a competing need to enable the portable power source to conveniently be recharged or otherwise supplemented and/or bypassed or replaced, if needed.

It is therefore a desired need to improve the state of the art of illuminators that are used in vaginal speculum assemblies and also to minimize at least some of the above stated problems confronted by the patient and caregiver in the use and operation of same.

SUMMARY OF THE INVENTION

According to one aspect, there is described an illuminator assembly comprising a portable illuminator containing a light source and a portable power source acting as a primary power source. The portable illuminator further includes an interface that is selectively engageable with an interface on at least two electrical devices, at least one of the electrical devices being used to at least one of supplement and replace the primary power source.

According to one version, one of the at least two electrical devices is a charging station that can recharge the primary power source (e.g., a rechargeable battery) of the illuminator. An electrical device interface is included in the charging station, the interface including a receiving port. The receiving port includes at least one engagement member, the at least one engagement member being biasedly disposed into the receiving port and engageable with the portable illuminator to provide a retaining fit when the portable illuminator is placed into the receiving port.

The portable illuminator includes a base portion that engages the at least one engagement member. The at least one engagement member includes a contoured surface that creates a camming action with the illuminator to move the at least one engagement member from a first position to a second position when the illuminator is inserted into the receiving port.

Preferably, the charging station includes a pair of engagement members, each of the pair of engagement members extending from opposing facing internal sides of the charging station. Each of the at least one engagement members is spring biased into the receiving port. At least one tube is disposed into which springs are placed for biasing the at least one engagement member in the first position. The illuminator is retained within the charging station when the at least one engagement member is moved to the second position.

The charging station includes circuitry for charging the primary power source of the portable illuminator when the illuminator is connected to the interface. The charging station includes a mechanism for selectively releasing the portable illuminator from the receiving port.

Another of the at least two electrical devices can, for example, include an auxiliary power module that can either temporarily bypass or supplement the primary power source. In either instance, each of these devices includes an interface that can selectively engage that of the illuminator.

Each of the interfaces of the at least two electrical devices and the illuminator includes at least one electrical contact. According to another version, one of the illuminator and electrical devices interfaces includes at least one lateral protrusion and the other of said interfaces includes a grooved portion to slidingly receive the at least one lateral protrusion.

The grooved portion can include an end wall to permit engagement between the interfaces in only one lateral direction.

According to a specific version, the illuminator interface includes a pair of ways that are disposed at lateral edges between a bottom surface and a recessed portion. Preferably, the pair of ways is angled, wherein each way is further defined by a pair of oppositely oriented angled lateral surfaces that are situated about a centerline of the interface. Each of the at least one pair of ways can also be inwardly angled with respect to a bottom or base surface of the illuminator.

According to another version, the illuminator interface is axially engageable with the interface of a first electrical device and is slidingly engageable with the interface of a second electrical device.

According to another aspect, there is described an illuminator assembly comprising a portable illuminator including an integrally contained light source and a rechargeable primary power source, a first electrical device, and a second electrical device, each of the first and electrical devices being separably engageable with said illuminator, wherein at least one of the first and second electrical devices recharges the primary power source and the other of said electrical devices at least one of supplements and replaces the portable primary power source.

In one version, each of the first and second electrical devices includes an interface for selectively engaging an interface of the portable illuminator. The interfaces of the electrical devices can be different interfaces that are commonly connectable to the interface of the illuminator. For example, one of the electrical devices can be a charging station and the other electrical device can be an auxiliary power source.

In one version, the interface of one of the first and second electrical devices axially engages the illuminator interface and the interface of the other of the first and second electrical devices slidingly engages the illuminator interface.

Preferably, the portable illuminator of the assembly is reusable and the speculum is disposable.

According to yet another aspect, there is described a charging station for a portable illuminator, the portable illuminator containing at least one portable power source. The charging station includes at least one receiving cavity having at least one engagement member biased in a first position that extends laterally into said receiving cavity and at least one electrical contact that engages a corresponding electrical contact of said illuminator when said illuminator is inserted into said receiving cavity, said at least one engagement member being moved to a position that retains said illuminator when said illuminator is inserted into said cavity.

The at least one engagement member is biased by at least one spring into the first position. The at least one spring can be damped, such as through use of a tubular member into which the at least one spring is disposed.

The at least one engagement member includes a contoured or beveled shape that permits the at least one engagement member to be cammed from the first position to a second position as the portable illuminator is inserted into the receiving port. In a preferred version, a pair of engagement arms extends into the receiving port from opposite facing internal sides of the port. The illuminator and engagement arms are shaped such that continued passage of a portion of the illuminator into the receiving port causes the arms to move back toward the first position, thereby retaining the illuminator in an upright and electrically engaged state.

According to still another aspect, there is provided an auxiliary power module for use with a portable illuminator, said portable illuminator including a primary power source and a portable light source. The auxiliary power module includes a plug that is releasably connectable to said illuminator to at least one of replace and supplement said portable power source.

The plug of the auxiliary power module includes an interface that is matingly engageable with an interface of the portable illuminator. Each of the interfaces includes at least one electrical contact. In one version, one of the illuminator and auxiliary power module interfaces includes at least one lateral protrusion and the other of said interfaces includes a grooved portion to slidingly receive the at least one lateral protrusion.

The grooved portion includes an end wall to permit engagement between the respective interfaces in only one lateral direction. One of the illuminator and auxiliary power module interfaces includes a pair of axially projecting areas and the other of said interfaces includes a pair of recesses sized to receive the axially projecting areas when the interfaces are slidingly engaged.

The interfaces include at least one pair of ways disposed at lateral edges of the axially projecting areas and the recesses. At least one of the pair of ways is angled. The at least one pair of ways include oppositely oriented angled surfaces situated about a centerline of the interfaces.

According to still another aspect, there is provided an illuminator assembly comprising a portable illuminator including an integrally contained light source and a primary power source disposed within a housing. The housing further includes an electrical interface that has an electrical contact, said electrical interface being axially engageable with a first electrical device interface and slidingly engageable with a second electrical device interface.

In one version, one of the electrical devices is used to recharge said primary power source of the illuminator and the other of the electrical devices is used to at least one of supplement and replace the primary power source. In one version, the primary power source cannot be recharged using an electrical device while the light source of the illuminator remains enabled.

An advantage is that the herein described portable illuminator includes a miniature light source that has a longer service life, is more shock tolerant, and dissipates less heat than those in previous devices of this type. In addition, making the illuminator portable enables the assembly to be versatile, for example, in remote locations wherein the profile of the illuminator and the handle portion of the speculum are sufficiently compact to enable greater ease of use between patients, for example bed-ridden patients.

Yet another advantage is that the portable illuminator can adaptively be connected to at least one electrical device to enable a contained power source to be supplemented and/or bypassed, as needed. The electrical device can include, for example, an auxiliary power source or a charging station, enabling versatility of the illuminator for use with a speculum assembly or as an examination light.

Yet still another advantage provided is that the portable illuminator includes an interface that enables the use of same with multiple electrical devices to permit recharging, supplementing and/or replacing of the power source of the illuminator.

Yet still another advantage is that the illuminator is powered such that the contained light source produces uniform illumination regardless of the operating voltage of the contained primary power source (e.g., whether the battery is charged or nearly depleted). The illuminator also advantageously includes a number of safety features that protect the patient and user.

These and other features and advantages will become readily apparent from the following Detailed Description which should be read in conjunction with the accompanying drawings.

BRIEF DESCRIPTION OF THE DRAWINGS

FIG. 9(*b*) is a partial view of the portable illuminator of FIGS. 1-3, as attached to an electrical device of FIG. 9(*a*), the latter being used to supplement and/or bypass the portable power source contained in the portable illuminator;

FIG. 15(*b*) is a top plan view of the charging station of FIG. 15(*a*);

FIG. 17 is a side view of the charging station of FIGS. 15(*a*)-16, having a portable illuminator retained therein;

FIG. 18(*a*) is a partial perspective view of the distal end of the light pipe of the vaginal speculum of FIGS. 4-6(*c*) in accordance with one embodiment; and FIG. 18(*b*) is a partial side view of the vaginal speculum of FIGS. 4-6(*c*), including the light pipe thereof.

DETAILED DESCRIPTION

The following embodiment details the use of a portable illuminator as used with a vaginal speculum assembly wherein the illuminator can also be independently used as an examination light. Various terms are used throughout to provide a suitable frame of reference with regard to the accompanying drawings such as "lower", "upper", "top", "bottom", "within", "lateral", "upon", "front", "back", and the like. Such terms are not intended to be overly limiting, however, except where so specifically indicated.

Figure 1:
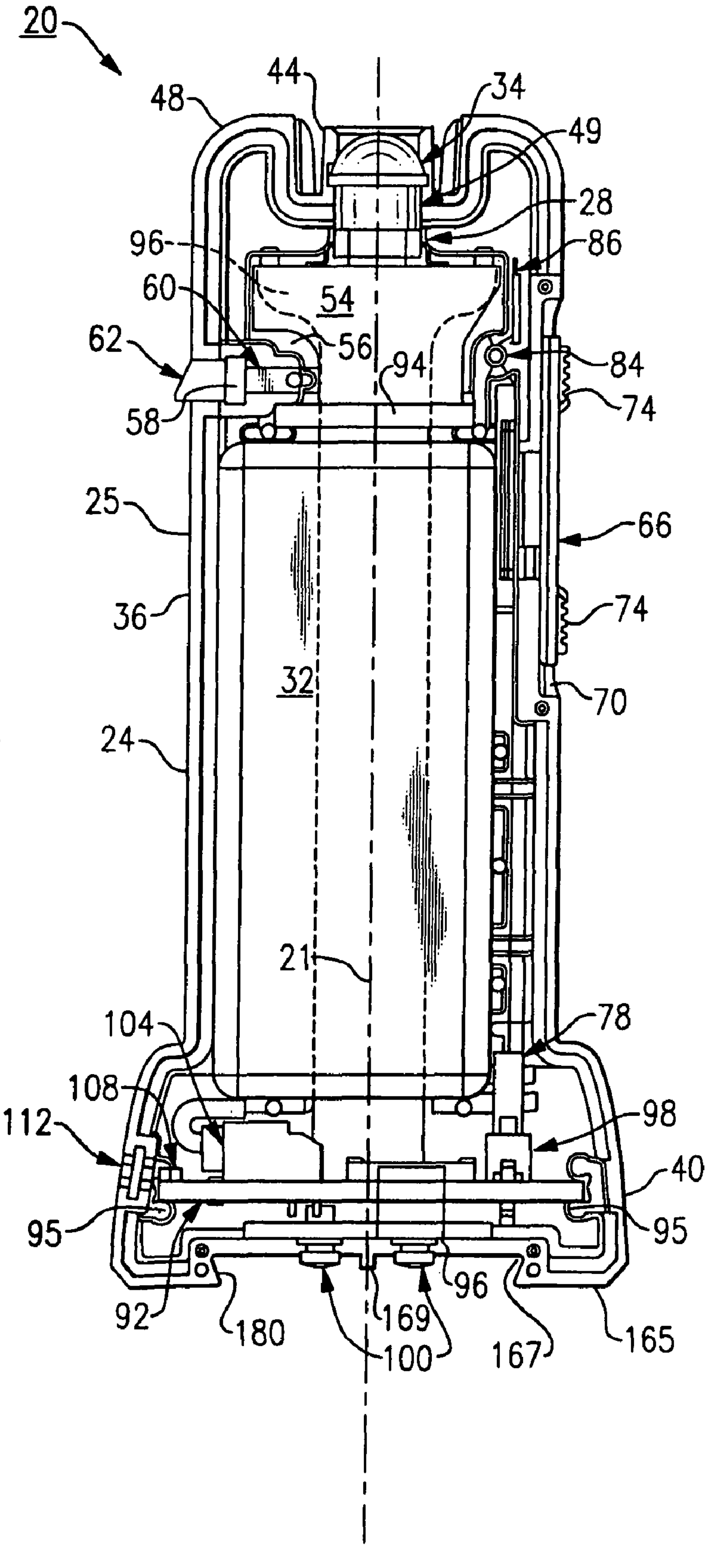
FIG. 1 is a side view of a portable illuminator, shown in section, made in accordance with an exemplary embodiment.

Referring to FIG. 1, there is shown a portable illuminator 20 that is defined by a housing or body section 24 having an interior sized to retain a number of components, including, among others, at least one portable light source and at least one portable power supply. According to the specific embodiment described herein, the portable light source is a white LED 28, such as, for example, those manufactured and sold by Nichia America, Inc. and Lumileds, Inc., while the portable power source includes at least one rechargeable battery 32, such as, for example, a Model UF612248PJFH lithium-ion battery manufactured by Sanyo Corp, the battery having suitable characteristics to sufficiently power the LED. Though the use of an LED is preferred, it should be noted that the design of the illuminator 20 is intended to make it "portable"; that is, such that it is not tethered and does not require a non-portable power source, such as a wall transformer or AC power supply, and wherein the illuminator functions as an integrated unit. To that end, it should be readily apparent that other forms of portable light sources, such as arc lamps and/or incandescent lamps, or other rechargeable power sources, such as other forms of batteries or alternative sources; such as, for example, capacitors capable of being recharged for portable use can be substituted.

According to this embodiment, the housing or body section 24 of the portable illuminator 20 is manufactured from a lightweight, durable material, such as a moldable plastic, and is further defined by an upper housing portion 36 and a lower base portion 40. The housing 24 according to the present embodiment is made from a two piece shell-like structure that is ultrasonically welded or otherwise connected together. Other forms of construction, however, should be readily apparent. For example and alternatively, a battery compartment could be provided having a removable cover (not shown), if desired, for removing and replacing the rechargeable battery 32 as needed.

Figure 3:
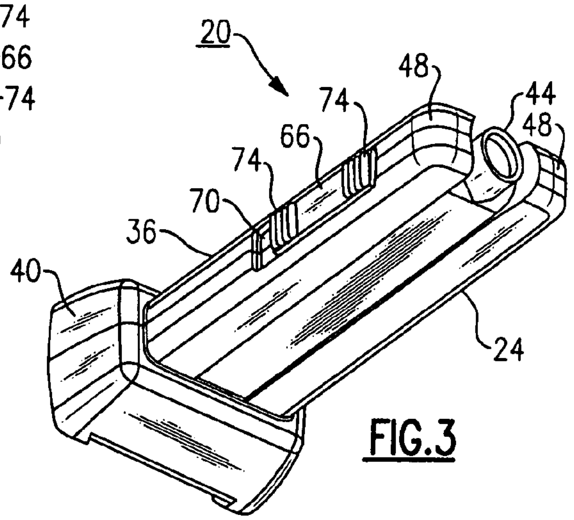
FIG. 3 is a top perspective view of the portable illuminator of FIGS. 1 and 2.

The upper housing portion 36 is defined by a relatively flat, thin section having a substantially constant thickness and width wherein each of these dimensions approximately equals that of the contained battery 32. According to this embodiment, the lower base portion 40 is significantly wider than that of the upper housing portion 36, the former expanding from a minimum width adjacent the bottom of the upper housing portion to a maximum width at the bottom thereof. The transition from the top to the bottom of the lower base portion 40 is in the form of a substantially trapezoidal shape, as viewed from the side of the illuminator 20; see for example, FIG. 3. This transition provides an ergonomic design and further assists in positioning and retaining the illuminator 20 in a charging station 250, FIG. 17, as described in greater detail below.

The LED 28, according to this embodiment, is retained within a substantially cylindrical region 44 projecting from the top of the upper housing portion 36. The cylindrical region 44 preferably surrounds the lens envelope (not shown) of the LED 28, as well as a front lens element 34, wherein the cylindrical projecting region protects both the LED and lens element from shock and impact loads.

The LED 28 is further housed within a retaining structure 49 wherein the electrical contacts of the LED are attached to a flexible circuit assembly 96, one end portion of which covers a heat sink 54 made from aluminum or other material with suitable heat conductivity properties that is disposed between the battery 32 and the LED 28, each being disposed within the upper housing portion 36. The remainder of the flexible circuit assembly 96 extends downwardly across one facing side of the illuminator 20 to the bottom of the lower base portion 40. The electrical contacts (not shown) extending from the LED 28 are attached to the flex circuit assembly 96 using a thermal epoxy, such as Emerson Cuming Stycast 2850, such that the contacts also conduct heat away from the LED 28 to the heat sink 54.

The retaining structure 49 can include an interior reflective surface (not shown) to assist in directing light towards the front lens element 34. According to this embodiment, the heat sink 54 includes a lateral recess 56 that permits the inclusion of a retention pin 58 having a beveled end 62 that extends outwardly from one lateral side 25 of the housing 24. The beveled end 62 of the retention pin 58 is biased outwardly by means of a spring 60. According to this embodiment, a spacer 94, having a layer of a soft foam material provided on upper and lower facing sides thereof, is disposed between the bottom of the heat sink 54 and the battery 32, this spacer providing isolation from shock and impact loads being applied to the illuminator 20.

As noted, a flexible or flex circuit assembly 96 is provided in relation to the LED 28, an upper end portion of the flexible circuit assembly being folded about the heat sink 54 and extending along the interior wide side of the illuminator 20. On the lateral side 25, FIG. 2, opposite the beveled retention pin 58, a slide switch 66 is vertically arranged within a slotted area 70 such that the switch is mainly recessed and does not extend outwardly beyond the exterior of the lateral side with the exception of a pair of tabs 74 disposed at respective ends of the exterior surface of the switch.

The slide switch 66 is biased in an off position by means of a switch spring 78 attached to a leaf spring 86 extending along substantially the entire lateral side of the housing 24. The leaf spring 86 is formed into a bump onto which a dowel pin 84 is disposed. The lower end of the leaf spring 86 is attached to the switch spring 78, the switch spring being further disposed in relation to a tactile switch 98 that is attached to the printed circuit board 92. Downward movement of the slide switch 66 from the off position, such as by means of finger pressure against one of the tabs 74, causes corresponding movement of the leaf spring 86 sufficient to cause the switch spring 78 to be loaded into compression to engage the tactile switch 98 and engaging same, thereby completing the electrical connection between the LED 28 and the battery 32 and energizing the LED. Additional movement of the slide switch 66 overcomes the detent provided by the dowel pin 84 to hold the switch in an energized position. Heat that is generated by the LED 28 and the flexible circuit assembly is dissipated by the heat sink 54.

In addition, the lower base portion 40 further retains a printed circuit board 92 that is supported horizontally (i.e., perpendicular to the major dimension of the battery 32) and retained by a pair of channels 95. The lower end portion of the flexible circuit assembly 96 is disposed in overlaying relation over the bottom of the printed circuit board 92, this portion of the flexible circuit assembly including a pair of integral electrical contacts 100 that extend outwardly from the bottom of the housing 24. Providing each of the electrical contacts 100 integrally on the flexible circuit assembly provides savings in terms of the overall space envelope of the illuminator 20.

With regard to the components included on the printed circuit board 92, the contacts 100 employ a bi-polar diode bridge, thereby enabling the illuminator 20 to be oriented relative to a suitable interface in any one of a number of ways with regard to at least one electrical device, as described in greater detail in a later portion. Additionally, the circuit board 92 includes a power conversion means, for example, a buck-boost constant current LED driver, such as a Model LTC 3453UF; which drives the LED with substantially constant current over the useful voltage limits of the contained battery 32 (e.g., 4.2 volts for a charged battery, 2.4 volts for a nearly depleted battery). Other means can be alternatively provided. A battery connector 104 is also connected to the top surface of the printed circuit board 92 and the battery 32, wherein the circuit board 92 further includes a safety or protection circuit to prevent shorting and over charging of the contained battery 32, such as, for example, a Model UCC 3952-PW-1, manufactured by Texas Instruments, Inc. In addition to the above and according to this embodiment, a current charge limiter is also included that prevents the illuminator from being charged by an electrical device connected to the contacts 100 while the illuminator 20 is enabled. A low-battery LED assembly 108 is also attached to the printed circuit board 92, including a window 112, disposed in a lateral side of the lower base portion 40, to indicate to a user when the contained battery 32 is either charged or in need of charge, such as, for example, through flashing or a change in color of the LED, in a manner that is known in the field. For example, the low-battery LED assembly 108 can illuminate one color through the window 112 when 10 minutes of "on" time remains and a second color when 5 minutes of "on" time remains. It should be readily apparent that other similar configurations can be contemplated.

The upper housing portion 36 further includes a pair of upper shoulders 48 spaced evenly apart from the cylindrical projecting region 44 on opposing lateral sides thereof. Each of the shoulders 48 extends upwardly, according to this embodiment, such that the top surface of each shoulder is substantially coplanar with or slightly above the top of the cylindrical projecting region 44. The shoulders 48 therefore provide an additional means to protect the portable illuminator 20, and particularly the contained LED 28 and lens element 34, from impact and shock loads. By including the shoulders and the foam spacer 94, and based on the compact design of the herein described illuminator, the illuminator 20 can withstand drops from as high as 4 feet.

Figure 4:
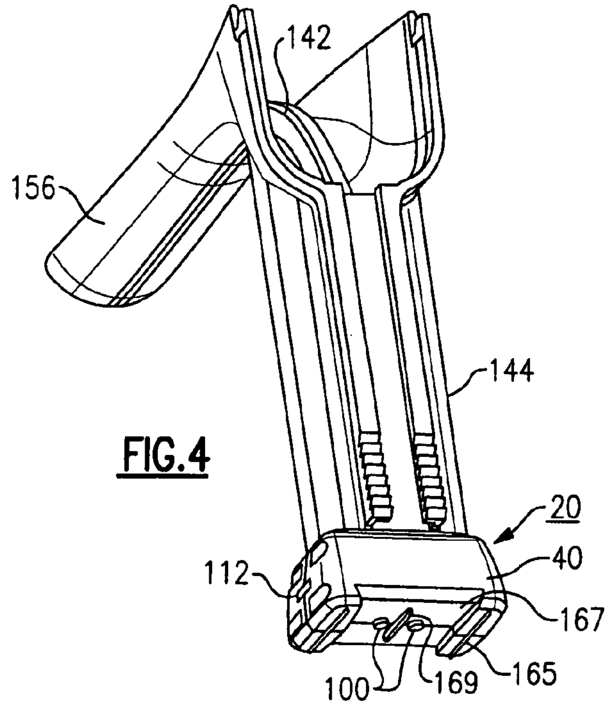
FIG. 4 is a bottom perspective view of the portable illuminator, as attached to a handle portion of a vaginal speculum.
Figure 5:
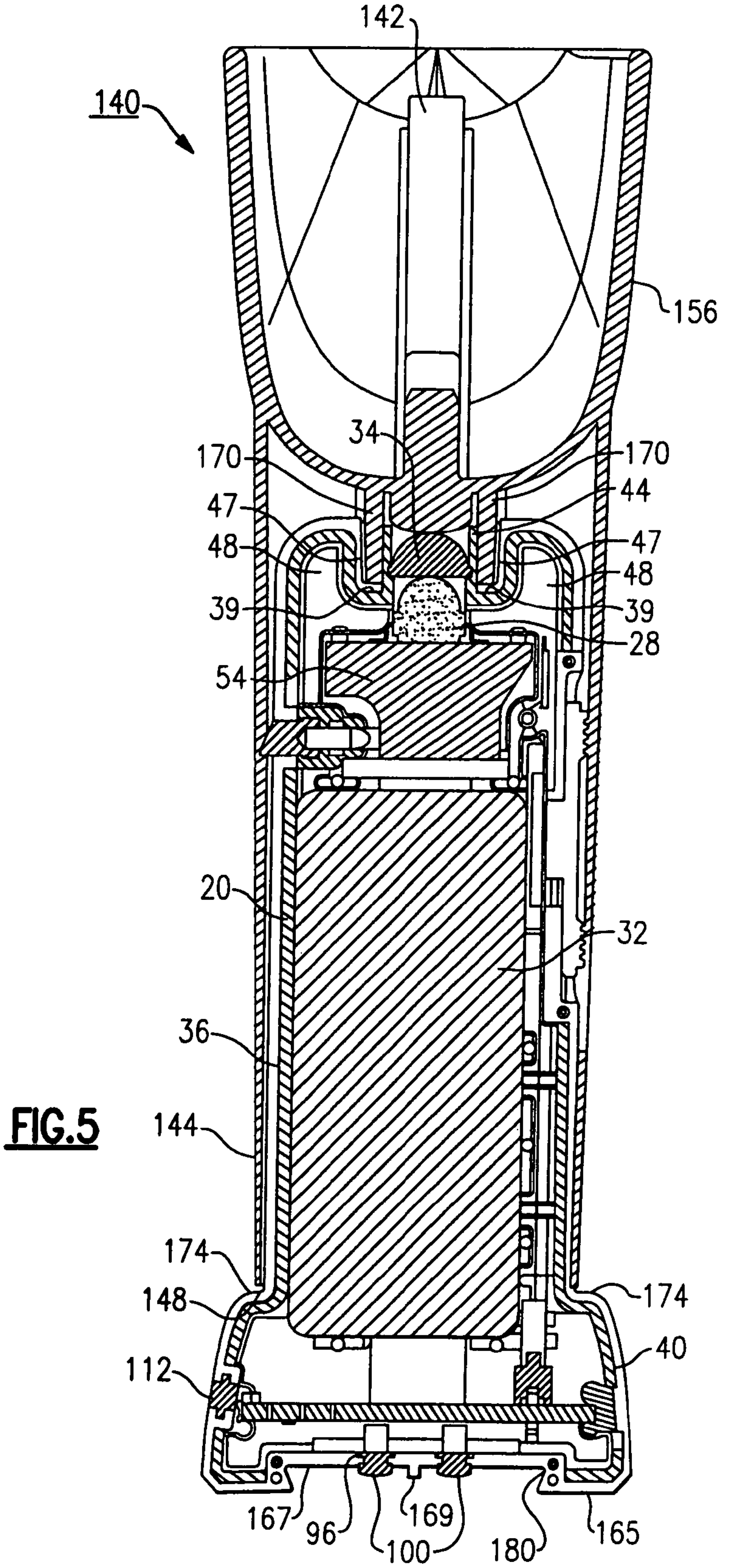
FIG. 5 is a sectioned elevational view of the vaginal speculum of FIG. 4 with the illuminator of FIGS. 1-3 inserted therein.

Referring to FIGS. 4 and 5, the upper housing portion 36 of the portable illuminator 20 is sized to be entirely fitted into the interior of a receiving cavity 148 of a handle portion 144 of a vaginal speculum 140. The contained LED 28 is optically coupled to a light pipe 142 having one end disposed in the proximal or upper end of the receiving cavity (not shown in FIG. 4, but shown more clearly in FIG. 18). Each of the upper housing and lower base portions 36, 40 are preferably contoured to facilitate cleaning, wherein the exterior profile of the lower base portion 40 is larger than that of the receiving cavity 148 of the vaginal speculum 140. When inserted into the receiving cavity 148, the window 112 is visible to a user.

Figure 6C:
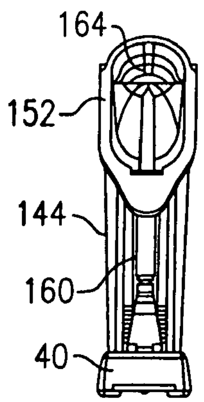
FIGS. 6(*a*), 6(*b*) and 6(*c*) are side, front and rear views, respectively, of the portable illuminator of FIGS. 1-3, as attached to a vaginal speculum.
Figure 6A:
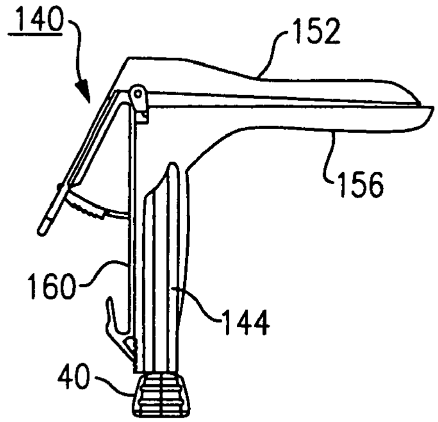
Figure 6B:
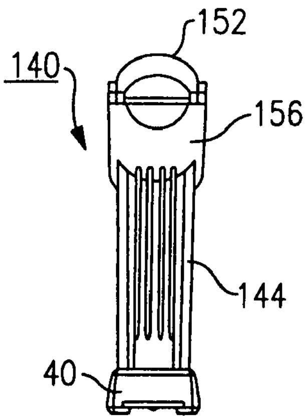

Referring briefly to FIGS. 5 and 6(*a*)-6(*c*), the vaginal speculum 140 used herewith is a disposable component that is manufactured preferably from an acrylic, polyamide or other suitable moldable plastic or other durable material. The speculum 140 is defined by an upper blade 152 and a lower blade 156 having the pistol-grip handle portion 144 that includes the receiving cavity 148. The rear of the upper blade 152 is attached to the upwardly extending fork of a yoke member 160 that is attached to the rear of the handle portion 144 of the speculum 140 to permit pivotal connection (angular articulation), as well as vertical elevation between the upper and lower blades 152, 156 in order to dilate the patient and provide an adequate viewing aperture 164 through the rear of the speculum 140.

Referring to FIGS. 18(*a*) and 18(*b*), the light pipe 142 is curved and extends from the upper end of the handle portion 144 along the interior of the lower blade 156. The proximal end 141 of the light pipe 142 includes a collecting lens 146 that is molded, according to this embodiment, as a center region in relation to a pedestal section contained within an annular gap formed between a set of centering fingers 170. At least one web or rib (not shown) is further provided to assist with moldability and to prevent the pedestal section from sagging about the collecting lens 146, the at least one rib improving material flow and gas removal around the lens. The purposes of the centering fingers 170 and collecting lens 146 with respect to an illuminator 20, FIG. 1, are discussed in greater detail in a succeeding portion of this description, wherein each provides improved optical coupling with the light source 28 of the portable illuminator 20.

The light pipe 142 receives light through the collecting lens 146 at the proximal end 141 and transmits light by means of internal reflection, wherein light is then emitted from the distal end 147. The distal end 147 of the light pipe 142 is preferably molded into the lower blade 156 of the speculum 140 and has a contoured configuration. By "contoured", what is meant is that the surface of the distal end has a defined shape that is not a 90 degree cut with respect to the axis of the light pipe 142. Therefore, it is intended that this term can cover both a range of angled surfaces, as well as curvi-linear surfaces, such as spherical, parabolic and the like. The contour of the distal end 147 is preferably formed as a scallop, such as would be cut by means of an end mill or similar apparatus. Alternatively, the above shape can be placed into the molding process for the lower blade 156 of the speculum 140, for example, if the speculum is being made from polystyrene, acrylic or other similar light transmissive materials.

The contour provided in the distal end 147 according to this particular embodiment is essentially a scalloped cut producing an inwardly (i.e., concave) curved portion or face having a radius of approximately 1.5 to 3.5 inches. The center of the radius is provided from a point Q, FIG. 18(*b*), which is approximately 2.6 inches, as measured distally from the rear or proximal side of the handle portion 144 and approximately 2.4 inches, as measured vertically from the top of the trough of the lower blade 156. These dimensions are shown in FIG. 18(*b*). It is noted that both dimensions locating the point Q for the herein described speculum 140 can be varied at least +/−0.030 inches and still produce a desirable effect. The herein described distal end 147 can alternatively be formed using an angled straight cut approximating that of the radiused scalloped end described above. According to one version, a suitable angle of approximately 70 degrees, as measured clockwise from the proximal upper end of the cut with respect to the perpendicular, FIG. 18(*b*), is provided, thereby creating a downwardly extending face. This angle can vary from approximately 55 degrees to approximately 80 degrees for purposes of providing improved illumination spot quality, while still reducing glare to the user. Each of the foregoing features is further described in greater detail in PCT Application No. PCT/US2006/12320, the entirety of which has previously been incorporated by reference. In addition to the foregoing, the herein described light pipe 142 includes a pair of lateral edges 149, which with respect to the sides of the radiused cut, are made essentially perpendicular to that of the face. Having relatively sharp edges 149 (i.e., radii less than or equal to 0.010 inches) provides an effective means of minimizing stray light. In addition and according to this embodiment, the face of the distal end 147 is polished and is also preferably treated with an optical finish, such as SP1 B1 to D3, in order further enhance light transmission.

In passing, it should be noted that the handle portion 146 of the herein described speculum 140 and the receiving cavity 148 are each sized to permit the selective inclusion of either a tethered illumination assembly or the portable illuminator 20. As such, the receiving cavity 148 includes features, for example, that require a tethered illumination assembly (not shown) to be insertable but only insertable in a single axial orientation that properly aligns the assembly with the collecting lens 146. More particularly, the receiving cavity 148 includes a pair of opposed rail-like portions formed between interior parallel sidewalls of the handle portion 144 and extending over substantially the length of the receiving cavity. These portions are used to align a tethered illumination assembly (not shown) and to allow the tethered assembly to be inserted into the handle portion 144 in either one of two 180 degree spaced rotational orientations. The rail-like portions also align with guide slots 37, FIGS. 2, 3, formed on the exterior of the upper housing portion 36 of the portable illuminator 36 to allow the assembly to be mounted in either of two 180 degree spaced rotational orientations.

The handle portion 144 according to this version is wider than previous versions to enable the upper housing portion 36 of the portable illuminator 20 to be fitted therein. As such, this handle portion 144 is defined by a larger aspect (width/depth) ratio that is ergonomically superior as well as actually being stronger than previous known versions, allowing thinner walled construction to provide similar or greater strength characteristics. According to this embodiment, the aspect ratio is about 2:1, although a range of about 1.25:1 to 3:1 is suitable to provide adequate stability and greater rigidity, while permitting hand-held operation. In addition, the front facing side of the handle portion 144 includes a plurality of exterior ribs 143, FIG. 6(*b*), that provide additional heat dissipation with regard to a contained illumination assembly by keeping a user's fingers away from "hot" surfaces wherein these ribs also additionally aid in manufacturability of the speculum 140 by providing material. Details relating to the retention and other above-noted features of the receiving cavity 148 and speculum 140 are described in greater detail in PCT/US2006/12116, previously incorporated by reference herein.

Figure 8:
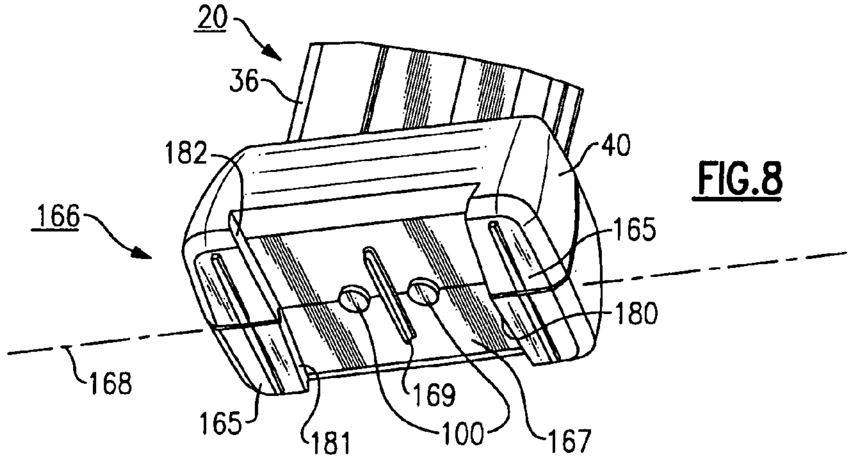
FIG. 8 is an enlarged bottom perspective view of the portable illuminator of FIG. 2.

Referring to FIGS. 1, 5 and 8, the bottom surface 165 of the portable illuminator 20 includes a recessed surface portion 167, defining an interface 166 that includes the pair of electrical contacts 100 extending outwardly therefrom. A transverse rib 169 is further provided between the pair of electrical contacts 100 in approximately the center of the bottom surface 165. A pair of side walls 180 defines the transition between the recessed surface portion 167 and the bottom or base surface 165 of the illuminator 20. Each of the side walls 180 is inwardly angled; that is, each side wall angles inwardly from the bottom surface 165 relative to the primary axis 21, FIG. 1, of the illuminator 20. In addition, each of the side walls 180 according to this embodiment further comprise a pair of angled segments 181, 182, FIG. 8, extending laterally outward relative to a centerline 168, FIG. 8, running perpendicular to the axis of the transverse rib 169.

Figure 9A:
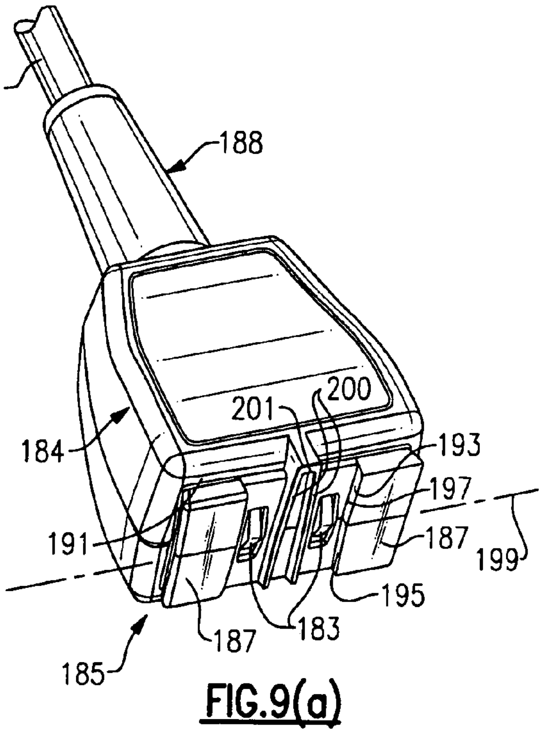
FIG. 9(*a*) is a partial perspective view of an electrical device having an interface that is engageable with that of the portable illuminator of FIG. 8.
Figure 9B:
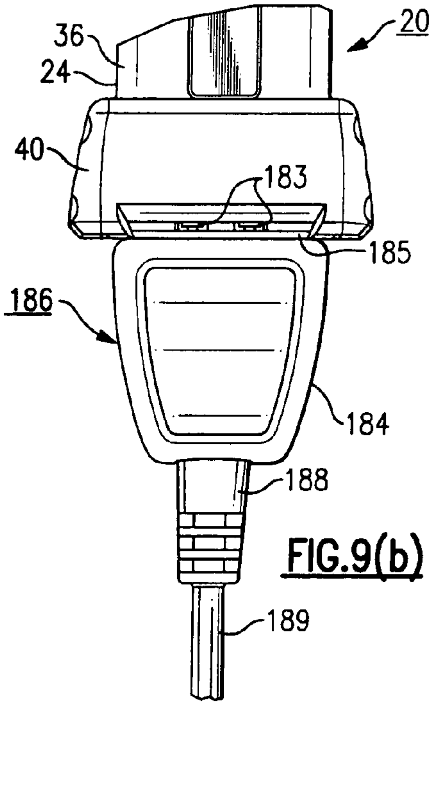

The bottom surface 165 and the recessed surface portion 167 of the lower base portion 40 of the portable illuminator 20, as described herein, define an interface 166 that can accommodate various electrical devices, a first such electrical device 186 being shown by way of example in FIGS. 9(*a*) and 9(*b*). According to this embodiment, the device 186 is an auxiliary power module (partially shown) that includes a plug 184 having a mating interface 185 corresponding to that of the portable illuminator 20. The plug 184 is relatively compact and ergonomic in design and includes a pair of exposed electrical contacts 183 that engage the electrical contacts 100 of the illuminator interface 166, the plug further having a strain relief 188 extending to a cable 189 further extending to a power source (e.g., an AC power supply—not shown) used to supplement and/or bypass or replace the battery 32, FIG. 1, which typically acts as the primary power source of the illuminator 20, FIG. 1. The design of the herein plug 184 actually utilizes a center mechanical contact (not shown) that is disposed between the exposed electrical contacts 183 and within the interior of the plug 184. Each of the contacts is spring biased, wherein the center contact provides an interior positioner.

Referring more particularly to FIG. 9(*a*), the module plug 184 includes a pair of axially extending areas or portions 187 extending from an end surface 191. Each of the axially extending areas 187 includes interior lateral walls 193, each of the latter being defined by oppositely oriented angled surfaces 195, 197 in relation to a centerline 199 of the interface. These angled surfaces 195, 197 engage with the oppositely oriented segments 181, 182 formed on the illuminator interface 166, each of which define respective dovetails on the illuminator 20 and plug 184 to allow engagement of the illuminator 20, FIGS. 8 and 9(*b*), from only one lateral direction relative to the auxiliary power module. Situated between the axially extending areas 187 and the electrical contacts 183 and centered therebetween are a pair of ribs 200 that upon assembly with the illuminator 20, surround the single transverse rib 169 of the illuminator 20, FIG. 9(*b*), in order to center the plug 184 of the auxiliary power module. The ribs 200 include an end wall or stop 201 that keeps the dovetail of the auxiliary power module plug 184 from jamming into the dovetail of the illuminator 20.

Figure 15A:
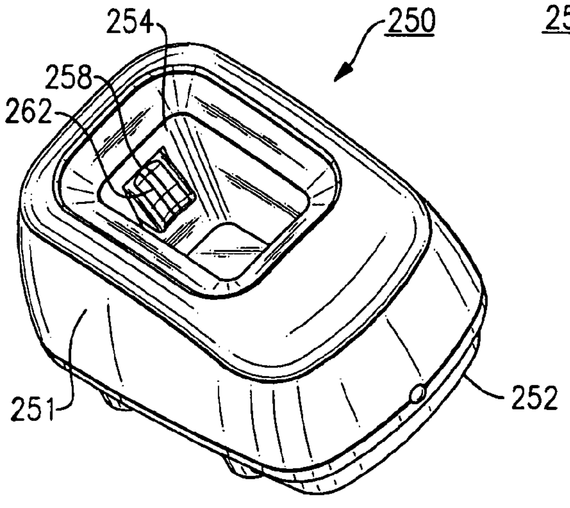
FIG. 15(*a*) is a top perspective view of a charging station used in connection with the portable illuminator of FIGS. 1-3.
Figure 15B:
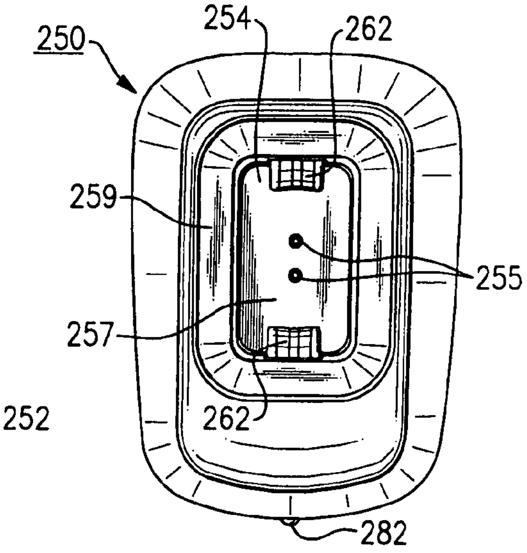
Figure 16:
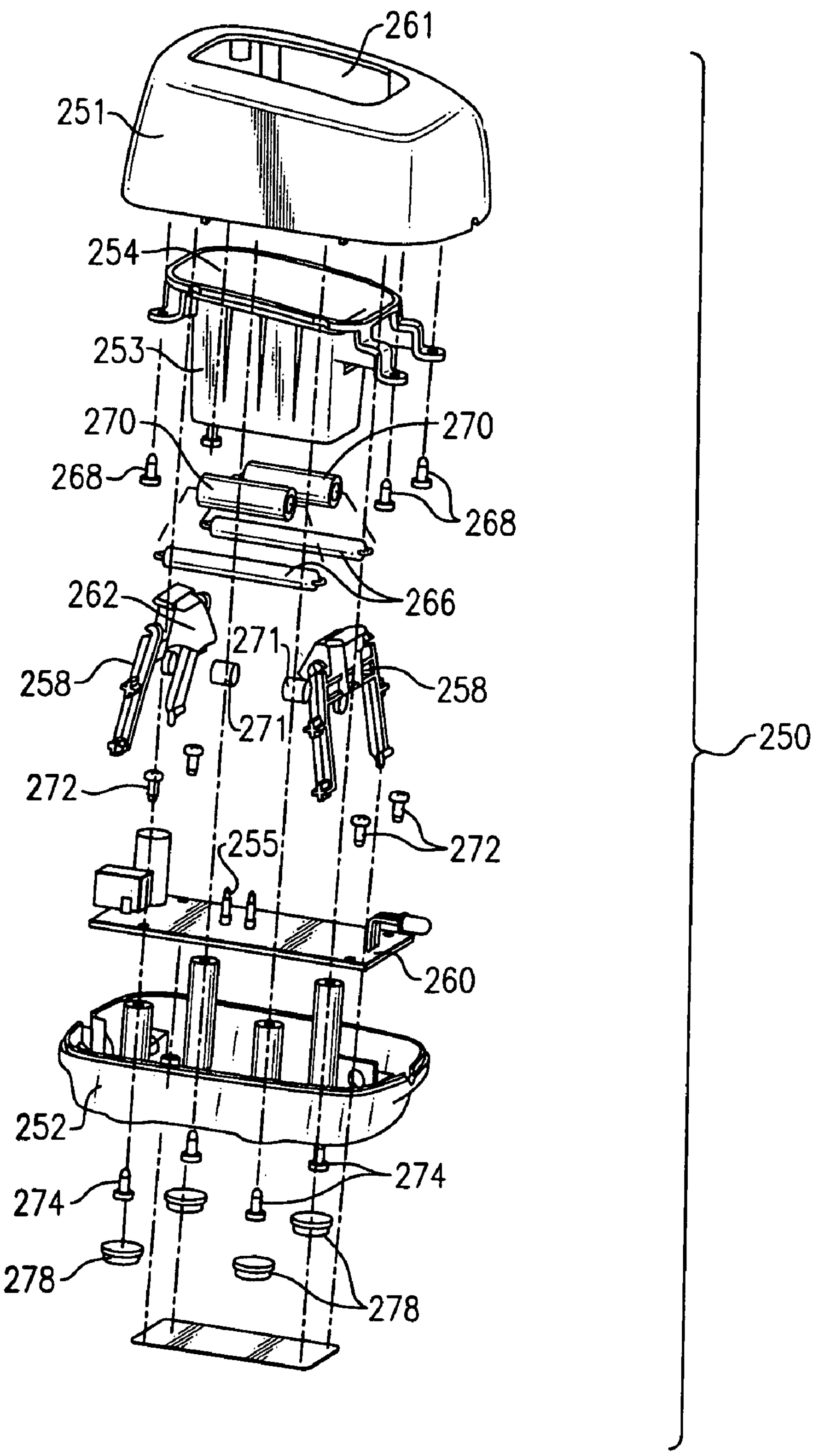
FIG. 16 is an exploded assembly view of the charging station of FIGS. 15(*a*) and (*b*)

The illuminator interface 166 is adapted to also be attachable to other electrical devices, such as, for example, a charging station or base 250, FIGS. 15(*a*)-17, the station having contained circuitry used to charge the battery 32, FIG. 1, of the illuminator 20 without having to remove the battery from the housing 24, FIG. 1, through selective coupling with the herein defined interface.

More particularly and referring to FIGS. 15(*a*)-17, the charging station or base 250 is defined by a unitary assembly that is constructed from an upper section 251 and a lower section 252, respectively, the charging station further including a number of components, including a receptacle 253 and a printed circuit board 260 sandwiched therebetween. The receptacle 253 includes a receiving port 254 that extends through an opening 261 formed in the upper section 251 to permit the passage of an illuminator 20, FIG. 17. The receiving port 254 includes an inwardly tapering top opening 259, FIG. 15(*b*), wherein the receptacle 253 is defined by a rectilinear cross section having a series of lateral or side surfaces, as well as a bottom surface 257. The printed circuit board 260 is disposed between the bottom surface 257 of the receptacle 253 and the lower section 252, the circuit board containing a plurality of components, including a pair of power input pins 255 that extend through the bottom surface 257 of the receptacle 253 into the receiving port 254.

A pair of engagement arms 258 includes contoured or beveled shaped ends 262 that are each biased into a first position that extends into the interior of the receiving port 254. Each of the engagement arms 258 is pivotally attached to the lower section 252 and is movable between a first position and a second position when an illuminator 20 is inserted into the receiving port 254. The engagement arms 258 are internally biased into the first position by use of springs 266, each of the springs being housed within respective tubular members 270 made from noise suppression material. In addition, pads 271, made from a similar noise suppression material, are provided within the interior of lateral side surfaces of the receptacle 253 and act as stops with regard to each of the engagement arms 258. Fasteners 268 and 274 are used to secure the receptacle 253 to the upper section 251 and the upper section 251 to the lower section 252, respectively. In addition, another set of fasteners 272 is used to secure the printed circuit board 260 in place relative to the lower section 252. A set of contact pads 278 is used to cover openings in the bottom surface of the lower section 252 into which the fasteners 274 are inserted, enabling the charging station 250 to be evenly positioned on a horizontal surface (not shown).

Figure 2:
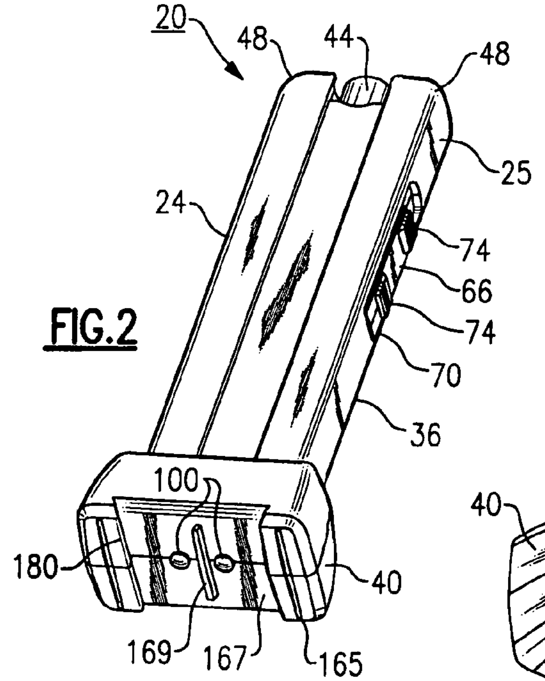
FIG. 2 is a bottom perspective view of the portable illuminator of FIG. 1.

As shown in FIG. 17, the lower base portion 40, FIG. 2, of the illuminator 20 is sized to be fitted into the receiving port 254 of the charging station 250. As the illuminator 20 is fitted therein, the beveled ends 262 are caused to move from the first position by engagement of the top of the beveled ends with the bottom of the lower base portion 40. As the remainder of the lower base portion 40 is pushed downwardly, the beveled ends 262 are caused to cam outwardly from the first position toward the second position. Once the top of the lower base portion 40 passes beneath the cammed beveled ends, there is no longer any force bearing upon the engagement arms 252 and the beveled ends are biased back toward the first position, thereby retaining the illuminator in place through the action of the beveled ends against the top of the lower base portion 40 and bringing the electrical contacts 100 and power input pins 255 into engagement. This engagement places pressure on the illuminator 20 to keep the illuminator upright and moreover to insure alignment for maintaining electrical connection with the charging station 250. Moreover and due to the geometry of the engagement arms 252 and of the lower base portion 40, the illumination assembly is self-orienting when fitted into the receiving port 254. The power input pins 255 of the charging station 250 are bi-polar according to this embodiment, therefore, the illuminator 20 can be positioned using either lateral orientation for charging. The illuminator 20 can be removed by pulling the upper housing portion 36 in an upward direction, wherein the tapering lower base portion 40 causes the beveled ends 262 to once again cam outwardly to the second position and allow the illuminator to be removed from the receiving port 254. The charging station 250 includes an exterior port (not shown) that permits connection to a power supply (not shown), as well as a charging LED 282 on an opposite lateral side thereof that indicates when charging of the battery 32, FIG. 1, contained within the illuminator 20 is complete. The LED 282, for example, can flash and/or change color, to indicate the status of charging. According to the present embodiment, the illuminator will not charge while it is operating; that is, the illuminator must be turned off before charging same for safety reasons.

Though the exemplary charging station 250 is shown with a single receiving port 253 and receptacle 254, it should be readily apparent that this device can include a plurality of receiving ports in order to accommodate a varied number of portable illuminators 20. Therefore, the illuminator 20, FIG.

1, can be recharged in any open port when indicated by the low-battery LED assembly 108, FIG. 1, as viewed through window 112, FIG. 1.

The illuminator and its interface therefore enables use of the illuminator as an independent portable examination light, as well as numerous applications, for example, with other medical devices. In addition, placing the electrical contacts 100 at the bottom of the illuminator interface 166, enables the contacts to remain clean when using the interface with either the auxiliary power module 186 and/or the charging station 250.

Figure 7A:
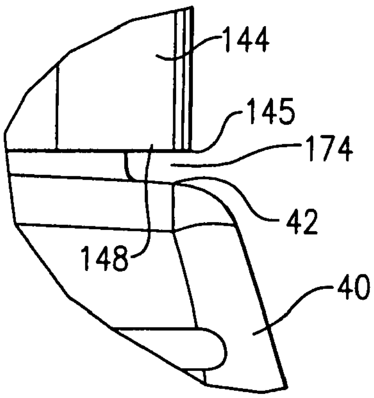
FIGS. 7(*a*) and 7(*b*) are enlarged views of FIGS. 6(*a*) and 6(*b*), respectively, illustrating a defined gap between an extending or lower base portion of the portable illuminator and the handle portion of the vaginal speculum.
Figure 7B:
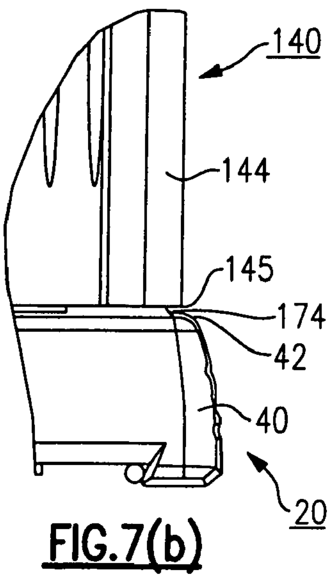

The following described aspects relate to the engagement of the portable illuminator 20 with the vaginal speculum 140. Referring to FIGS. 2 and 5, the shoulders 48 and the substantially cylindrical projecting region 44 of the portable illuminator 20 define respective lateral spacings 47 therebetween that are sized to accommodate the set of centering fingers 170, the latter also being depicted in FIG. 18(*b*), that extend downwardly (i.e., toward the open end) of the receiving cavity 148 of the speculum 140. The centering fingers 170 engage the spacings 47 when an illuminator 20 is inserted into the receiving cavity 148, wherein the fingers contact the top surface 39 of the upper housing portion 36, and permit the illuminator 20 to be inserted only to a predetermined distance. This engagement creates a gap 174 that is formed, as shown most particularly in FIGS. 7(*a*) and 7(*b*), between the nearest surface 42 of the extending lower base portion 40 and the end 145 of the handle portion 144. According to this embodiment, the defined gap 174 is no less than 0.020 inches.

In operation and when the portable illuminator 20 is inserted into the receiving cavity 148 of the speculum 140, the sliding switch 66 is automatically moved from the off position to a position that energizes the LED 28. In the meantime, the spring-loaded retention pin 58 provides a bearing force against the interior side wall of the receiving cavity 148 through its beveled end 62. This bearing force is sufficient to retain the illuminator 20 in place, but does not prevent removal of same from the receiving cavity 148 by a user. Additional details relating to this "automatic on" feature of the portable illuminator 20 and the retention of the illuminator in the receiving cavity 148 of the vaginal speculum 140 are described in co-pending Application No. PCT/US2006/12320, the entire contents of which are herein incorporated by reference.

Figure 10:
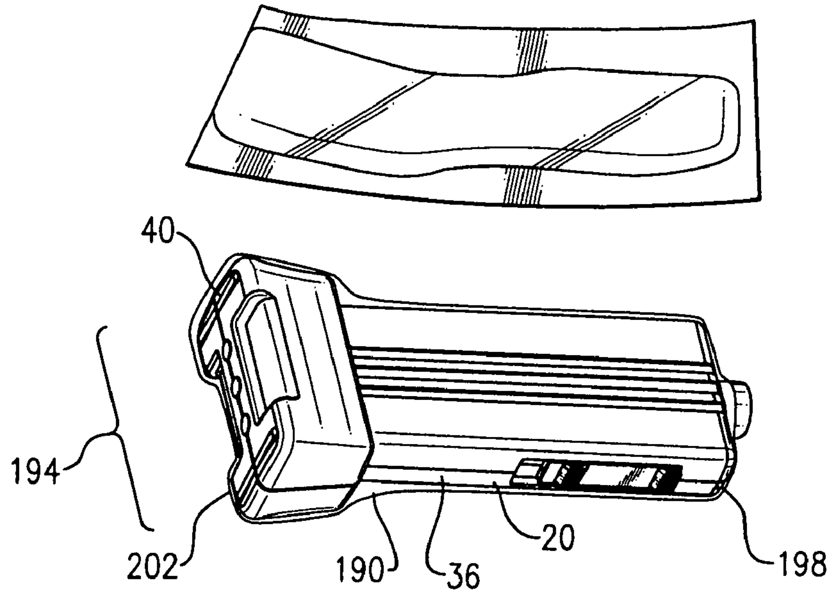
FIG. 10 is a perspective view of the portable illuminator of FIGS. 1-3 having a disposable sheath member according to a first design attached thereover.
Figure 11:
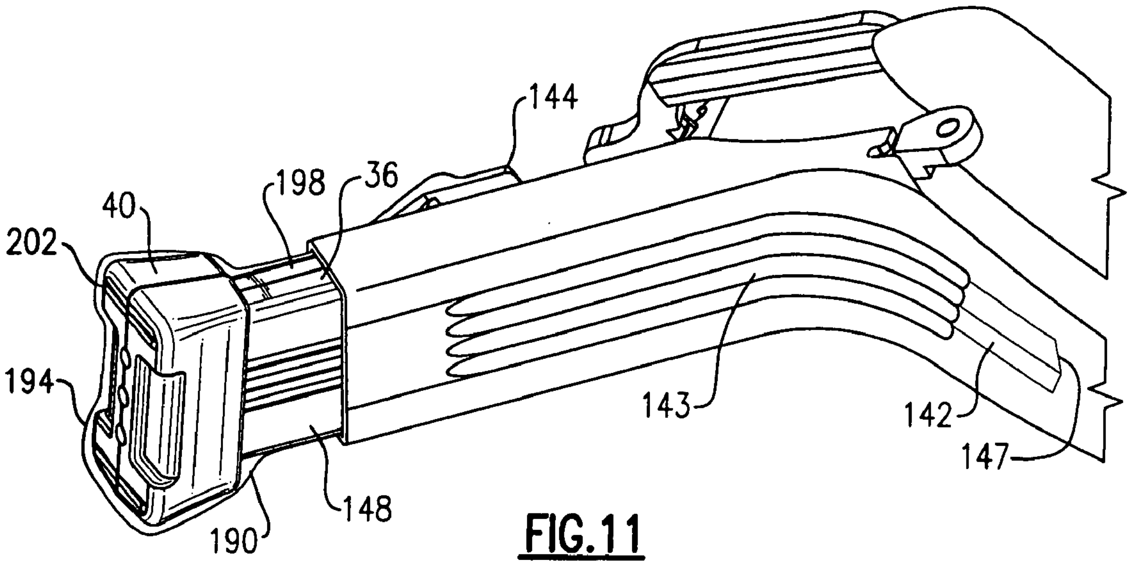
FIG. 11 is a perspective view of the illuminator with the attached sheath member of FIG. 10, as partially inserted into the receiving cavity of a vaginal speculum.
Figure 12:
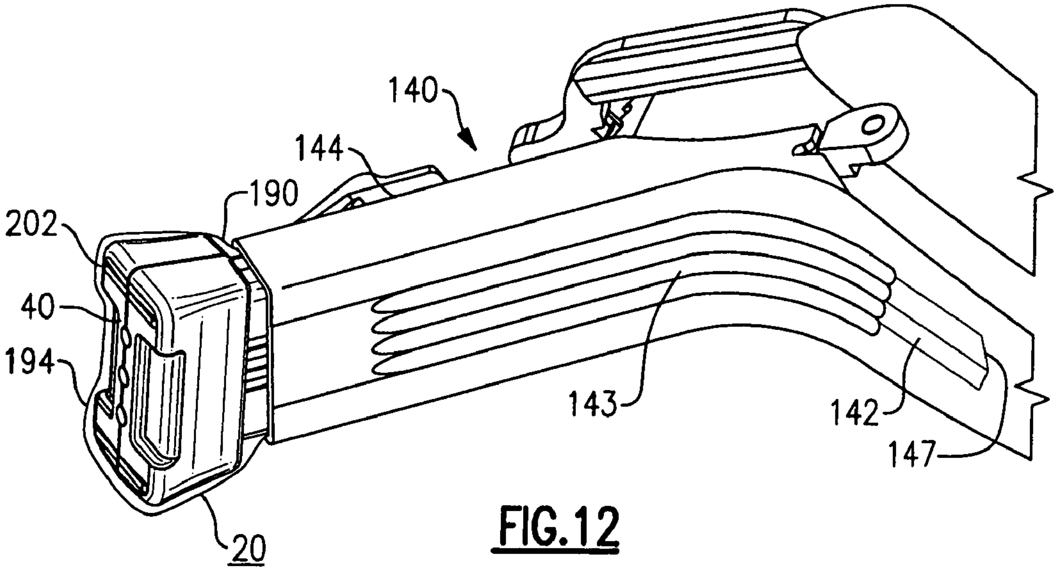
FIG. 12 is the perspective view of FIG. 11 with the portable illuminator and sheath member fully inserted into the receiving cavity.

Referring to FIGS. 11 and 12, the defined gap 174 permits the attachment of the herein described portable illuminator 20 relative to the receiving cavity 148 of the vaginal speculum 140, creates optical alignment (i.e., the proper axial spacing) between the contained light source and the light pipe, and further permits the attachment of a disposable sheath member 190. The sheath member 190 is preferably made from a thin film-like and highly flexible plastic material, such as polyethylene, that is wholly enclosed with the exception of an open lower end 194. The sheath member 190 according to this embodiment is defined by an upper portion 198 having a length and width dimension that is sized to entirely accommodate the upper housing portion 36 of the portable illuminator 20 and a lower portion 202 similarly sized to wholly enclose the lower base portion 40, as shown in FIGS. 10 and 11, wherein the illuminator 20 is placed into the highly flexible sheath member through the open lower end 194.

The portable illuminator 20 and attached sheath member 190 can then be inserted into the receiving cavity 148 of a vaginal speculum 140, as shown in FIG. 11 and FIG. 12, wherein each of the illuminator and attached sheath member is retained by corresponding features provided on the exterior of the illuminator and the interior of the receiving cavity. As in the instance when no sheath member is present, the sliding switch 66 is caused to automatically energize the contained LED 28 when the illuminator 20 is inserted to the predetermined position within the receiving cavity in that the slide switch is caused to move from the biased off position to an on or energized position. As previously noted, the switch 66 is spring biased and therefore removal of the portable illuminator 20 from the receiving cavity 148 will cause the switch to slide back to the biased off position. Additional details concerning this feature in accordance with one embodiment are described in previously incorporated PCT Patent Application No. PCT/US06/12320.

Due to the size of the defined gap 174, which as previously noted is at least 0.020 inches according to this embodiment, the disposable sheath member 190 can be used to protect the portable illuminator 20 from cross contamination, while still providing an anti-snagging feature with respect to a user's gloves (not shown) or fingers while inserting and removing the illuminator from the speculum 140. Similarly, the slide switch 66, due to its recessed position within the slot 70 of the illuminator 20, also provides a similar anti-pinch or anti-snag means in the event the portable illuminator is used independently as an examination light.

The sheath member 190 can be made entirely from a light transmissive material, such as clear polyethylene, or can include a window portion (not shown) in the upper portion thereof to permit light from the contained LED 28 to be transmitted without interference to the light pipe of the speculum 140. Alternatively, the sheath member 190 could be colored in order to filter the light transmitted by the illuminator 20 to the tissue or otherwise be treated in order to modify the characteristics of the transmitted light. This coloring or treatment would allow the caregiver to use the illuminator 20 without modification for varying the spectrum of the transmitted light, for attenuating the transmitted light, or for changing the geometric distribution of the transmitted light. One example of a varied spectrum is producing the effect of "red-free" illumination for cervical examinations. Alternatively and rather than including a colored sheath member to permit various light modification, the vaginal speculum, including the light pipe, can be tinted, for example, during the molding process thereof to achieve the same purpose with regard to light filtering and/or attenuation.

Figure 13:
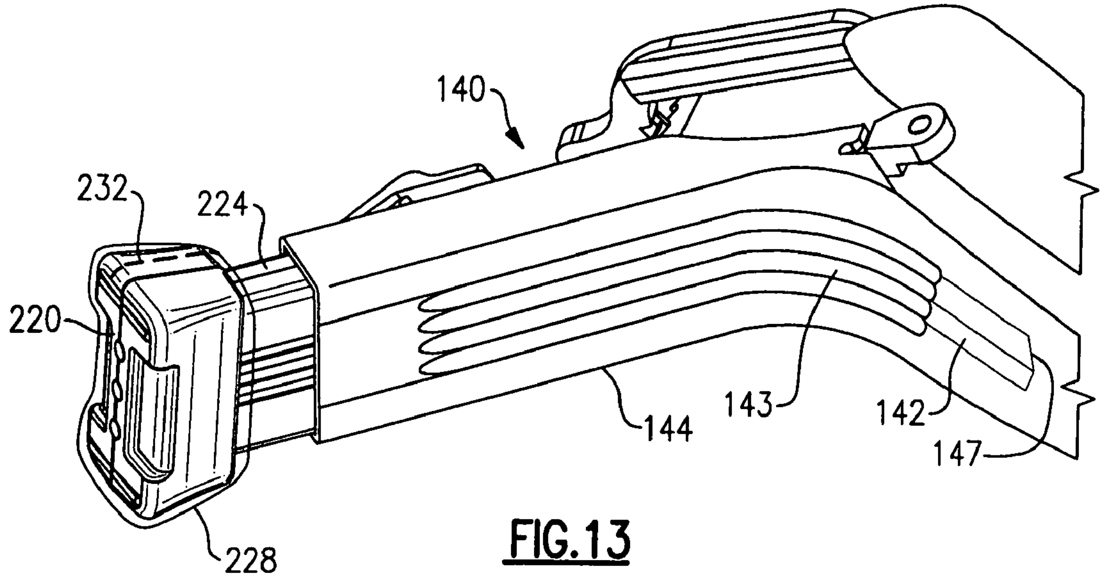
FIG. 13 is a perspective view of the portable illuminator of FIGS. 1-3 having a sheath member made in accordance with a second design that is attached over only an extending portion of a portable illuminator in relation to a vaginal speculum.

A second design of a disposable sheath member 220 is shown in FIG. 13. According to this embodiment, the sheath member 220 is sized to conform to only the lower base portion 40 of the portable illuminator 20. The sheath member 220 is made from a semi-rigid plastic material, such as polypropylene or polyethylene, and is defined by an open upper end 224 sized to conform with the tapered end of the lower base portion 40 of the illuminator 20, with the remainder of the sheath member having a substantially trapezoidal shape 228 that very closely conforms to and encloses the exterior of the lower base portion. When attached, the sheath member 220 is difficult to remove due to its close contacting fit with the lower base portion 40. Therefore, the sheath member 220 further includes at least one perforated tear strip 232 to enable release of same from the lower base portion 40 of the portable illuminator 20 when a patient examination is complete.

Figure 14:
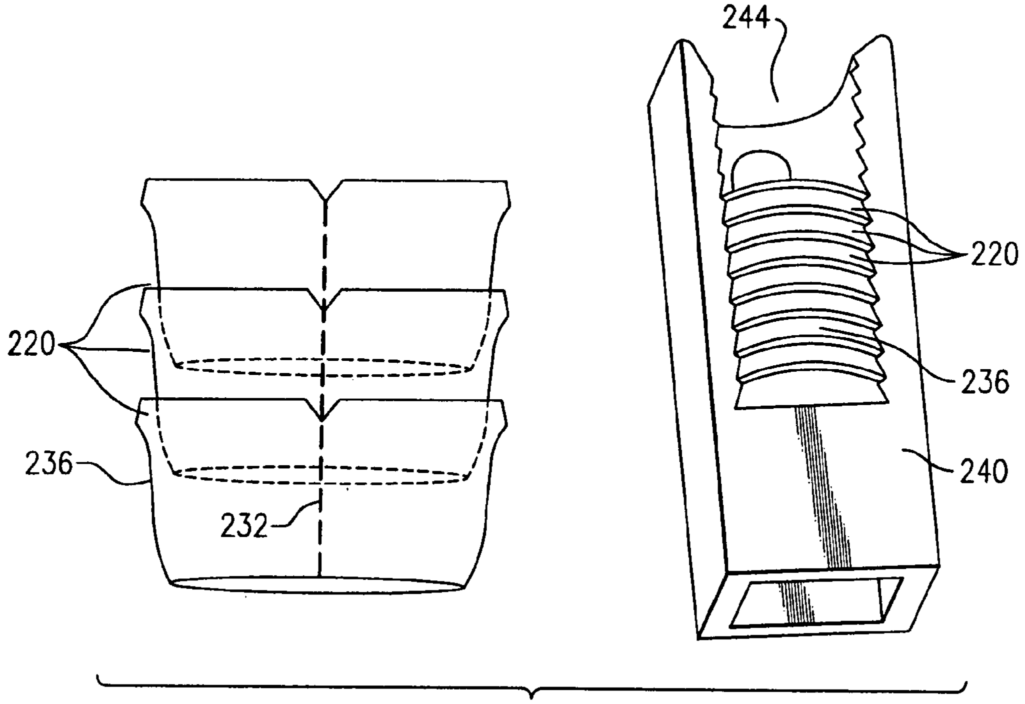
FIG. 14 depicts a stacked supply of the sheath members of FIG. 13 that can be dispensed individually onto a portable illuminator.

Referring to FIG. 14, the sheath members 220, due to their shape and rigidity, can be arranged in a stacked configuration 236 and stored in a sheath supply container 240. The sheath supply container 240 is defined by a box-like structure that includes an open end 244 to permit individual dispensing of the sheath members 220, as needed. A sheath member 220 can be dispensed by sliding the upper housing portion 36 of a portable illuminator 20 through the open end 244 of the stacked configuration 236 within the supply container 240 and pushing the supply container downwardly such that a sheath member 220 is fitted over the lower base portion 40. The portable illuminator 20 can then be removed from the supply container 240 with a sheath member 220 being secured thereto.

PARTS LIST FOR FIGS. 1-18(*b*)

20 portable illuminator
21 primary axis, illuminator
24 housing or body section
25 lateral side
38 portable light source (LED)
32 portable power source (rechargeable battery)
34 front lens element
36 upper housing portion
37 guide slots
39 top surface
40 lower base portion
42 nearest surface
44 substantially cylindrical region
47 spacings
48 upper shoulders
49 retaining structure
54 heat sink
56 lateral recess
58 retention pin
60 spring, pin
62 beveled end
66 slide switch
70 slotted area
74 tabs
78 spring, switch
84 dowel pin
86 leaf spring
92 printed circuit board
94 foam spacer
95 channels
96 flexible circuit assembly
98 tactile switch
100 extending electrical contacts
104 battery connector
108 low battery LED assembly
112 window
140 speculum, vaginal
141 proximal end, light pipe
142 light pipe
143 exterior ribs
144 handle portion
145 end, handle portion
146 collecting lens
147 light emitting end, contoured
148 receiving cavity
149 lateral edges
152 upper blade
156 lower blade
160 yoke member
164 viewing aperture
165 bottom surface
166 interface, illuminator
167 recessed portions
168 centerline
169 transverse rib
170 fingers
174 gap
180 side walls
181 angled segment
182 angled segment
183 contacts, electrical
184 plug
185 mating interface
186 electrical device (auxiliary power module)
187 axially extending areas or portions
188 strain relief
189 cable
190 sheath member, disposable
191 end surface
193 interior lateral walls
194 open lower end
195 oppositely oriented angled surface
197 oppositely oriented angled surface
198 upper portion
199 centerline
200 ribs
201 end wall or stop
202 lower portion
220 sheath member, disposable
224 open upper end
228 trapezoidal shape
232 tear strip, perforated
236 stacked configuration
240 sheath supply container
244 open end
250 charging station or base
251 upper section
252 lower section
253 receptacle
254 receiving port
255 power input pins
257 bottom surface
258 engagement arms
259 tapered top opening
260 circuit board, printed
261 opening
262 beveled or contoured end
266 springs
268 fasteners
270 tubular members
271 pads
272 fasteners
274 fasteners
278 contact pads
282 charging LED It will be readily apparent that there are numerous modifications and variations to those skilled in the field that is possible within the intended nature and scope of the apparatus, as described herein. For example and though the preceding embodiment has been described in terms of a specific disposable speculum, it is anticipated that this component could be reusable. Alternatively still, the illuminator herein described could be used in conjunction with other medical diagnostic instruments, for example, such as a laryngoscope, an anoscope, or other device. The illuminator can also be used independently as an examination light, using the herein described electrical interfaces to supplement, replace and/or recharge the power source of the illuminator.

In addition and though the exemplary embodiment is made in terms of a disposable speculum, it is anticipated that the illuminator and interface described herein could also be commonly used with a reusable (e.g., metal) speculum. In another instance, for example, the light pipe described herein could be separably attached to the interior of a metal speculum and the illuminator could be attached thereto to illuminate a medical target (e.g., the cervix).

The invention claimed is:

1. An illuminator assembly for a medical device having a receiving cavity, the illuminator assembly comprising:

a portable illuminator containing a light source and a portable power source acting as a primary power source, said illuminator further including a housing having an upper portion and a lower base portion, said lower base portion of said portable illuminator further including a single end interface that is selectively engageable with at least two electrical devices wherein said single end interface axially engages one of said at least two electrical devices in a direction which extends along a primary axis of said illuminator, said primary axis being co-extensive with said upper and lower base portions of said illuminator and the other of said at least two electrical devices slidingly engages said single end interface of said illuminator in a direction which is nonaxial and substantially orthogonal to said axial direction, said interface including a set of contact pins extending from a recessed surface portion of said lower base portion that are commonly engaged by either of said electrical devices, said upper portion of said illuminator further including a lens element and a retention pin, the retention in biased outwardly from the upper portion by a spring to provide a bearing force against the cavity when the upper portion is engaged with the cavity.

2. An illuminator assembly as recited in claim 1, wherein the lower base portion is engaged with one of said at least two electrical devices and wherein one of said at least two electrical devices is an auxiliary power source.

3. An illuminator assembly for a medical device having a receiving cavity, the illuminator assembly comprising:

a portable illuminator containing a light source and a portable power source acting as a primary power source, said illuminator further including a housing having an upper portion and a lower base portion, said lower base portion of said portable illuminator further including a single end interface that is engageable with a charging station wherein said single end interface axially engages said charging station in a direction which extends along a primary axis of said illuminator, said primary axis being co-extensive with said upper and lower base portions of said illuminator, said interface including a set of contact pins extending from a recessed surface portion of said lower base portion that are engaged by said charging station, said upper portion of said illuminator further including a lens element and a retention pin, the retention pin biased outwardly from the upper portion by a spring to provide a bearing force against the cavity when the upper portion is engaged with the cavity.

4. An illuminator assembly as recited in claim 3, wherein said charging station includes a receiving port sized to receive said lower base portion.

5. An illuminator assembly as recited in claim 4, wherein said receiving port includes at least one engagement member, said at least one engagement member being biasedly disposed into said receiving port and engageable with the lower base portion of said portable illuminator to provide a retaining fit when said portable illuminator is placed into the receiving port.

6. An illuminator assembly as recited in claim 5, wherein said at least one engagement member includes a contoured surface that creates a camming action with said illuminator to move said at least one engagement member from a first position toward a second position as said illuminator is inserted into said receiving port.

7. An illuminator assembly as recited in claim 6, wherein each of said at least one engagement members is spring biased into a first position laterally extending into said receiving port.

8. An illuminator assembly as recited in claim 7, including at least one tube into which springs for biasing said at least one engagement member are disposed.

9. An illuminator assembly as recited in claim 8, wherein said tube is made from a noise suppressing material.

10. An illuminator assembly as recited in claim 6, wherein said portable illuminator is retained in said charging station when said at least one engagement member moves from the second position toward the first position.

11. An illuminator assembly as recited in claim 5, including a pair of engagement members, each of said pair of engagement members extending from opposite facing internal sides of said charging station.

12. An illuminator assembly as recited in claim 4, wherein said charging station includes a mechanism for selectively releasing said portable illuminator from said receiving port.

13. An illuminator assembly as recited in claim 3, wherein said electrical device interface is included in said charging station and wherein said charging station includes circuitry for charging said portable primary power source of said portable illuminator when said illuminator is connected to said receiving port.

14. An illuminator assembly for a medical device having a receiving cavity, the illuminator assembly comprising:

a portable illuminator containing a light source and a portable power source acting as a primary power source, said illuminator further including a housing having an upper portion and a lower base portion, said lower base portion of said portable illuminator further including a single end interface that is engageable with a plug wherein said single end interface slidingly engages said single end interface of said illuminator in a direction which is nonaxial and substantially orthogonal to said axial direction, said interface including a set of contact pins extending from a recessed surface portion of said lower base portion that are engaged by said plug, said upper portion of said illuminator further including a lens element and a retention pin, the retention pin biased outwardly from the upper portion by a spring to provide a bearing force against the cavity when the upper portion is engaged with the cavity.

15. An illuminator assembly as recited in claim 14, wherein said plug includes at least one lateral protrusion and a bottom surface of said illuminator interface includes a grooved portion sized to slidingly receive said at least one lateral protrusion.

16. An illuminator assembly as recited in claim 15, wherein said grooved portion includes an end wall to permit engagement between said interfaces in only one lateral direction.

17. An illuminator assembly as recited in claim 14, wherein one of said bottom surface of said portable illuminator and said plug includes a pair of axially projecting areas and the other of said interfaces includes a pair of recesses sized to receive said axially projecting areas when slidingly engaged therewith.

18. An illuminator assembly as recited in claim 17, wherein said interfaces include at least one pair of ways disposed at lateral edges of said axially projecting areas and said recesses.

19. An illuminator assembly as recited in claim 18, wherein said at least one pair of ways are angled.

20. An illuminator assembly as recited in claim 19, wherein said at least one pair of ways include oppositely oriented angled surfaces situated about a centerline of said interfaces.

21. An illuminator assembly for a medical device having a receiving cavity, the illuminator assembly comprising:

a portable illuminator including a housing including an upper portion and a lower base portion, said housing retaining an integrally contained light source and a portable primary power source, said upper portion of said illuminator further having a lens element and a retention pin, the retention pin biased outwardly from the upper portion by a spring to provide a bearing force against the cavity when the upper portion is engaged with the cavity;

a first electrical device; and a second electrical device, wherein each of said first and second electrical devices are selectively engageable with said illuminator wherein in which one of said first and second electrical devices recharges said portable primary power source and the other of said first and second electrical devices at least one of supplements and replaces said portable primary power source wherein each of said first and said second electrical devices includes an electrical interface for selectively engaging an electrical interface of said portable illuminator defined by said lower base portion, said electrical interface of said portable illuminator having a set of electrical contacts extending from a recessed portion of said illuminator, each of said first and second electrical devices including different interfaces that are each commonly and selectively connected to said set of electrical contacts of the electrical interface of said illuminator wherein one of said electrical interfaces of one of said first and second electrical devices axially engages receives the electrical interface lower base portion of said illuminator and the other of said electrical interfaces of said first and second electrical devices nonaxially engages the bottom surface of said illuminator electrical interface, each of said interfaces being engageable with the set of electrical contacts extending from the bottom surface of said illuminator.

22. An illuminator assembly as recited in claim 21, wherein said first electrical device is a charging station and said second electrical device is an auxiliary power source.

23. An auxiliary power module with a portable illuminator, said portable illuminator including a primary power source, an upper portion having a lens element and a retention pin, the retention pin biased outwardly from the upper portion by a spring to provide a bearing force against a receiving cavity of a medical device when the upper portion is engaged with the cavity, a portable light source disposed in a housing and an electrical interface defined at a bottom surface of said illuminator, said auxiliary power module including a plug that is releasably and slidingly connectable to the bottom surface of said illuminator to at least one of replace and supplement said primary power source, said bottom surface having at least one recessed electrical contact that is engaged when connected to corresponding electrical contacts of said plug, wherein said auxiliary power module includes at least one lateral protrusion and the bottom surface includes a grooved portion sized to slidingly receive said at least one lateral protrusion, the direction of sliding being orthogonal to that of a primary axis of said illuminator wherein said interface is further selectively axially engageable with at least one other electrical device without modification thereto.

24. The auxiliary power module as recited in claim 23, wherein the grooved portion is sized to receive a center transverse rib of the engaged interface, said grooved portion having an end wall to permit engagement between the interfaces in only one lateral direction relative to the interface having said end wall.

25. The auxiliary power module as recited in claim 23, wherein said plug of said auxiliary power module includes a strain relief.

26. An illuminator assembly for a medical device having a receiving cavity, the illuminator assembly comprising:

a portable illuminator including an upper portion having a lens element and a retention pin, the retention pin biased outwardly from the upper portion by a spring to provide a bearing force against the cavity when the upper portion is engaged with the cavity, an integrally contained light source and a primary power source each disposed within a housing, said housing further including an electrical interface defined by a lower base portion of said housing and having at least one common electrical contact, said electrical lower portion including a bottom surface that is axially engageable with a first electrical device interface and slidingly engageable with a second electrical device interface, wherein the direction of slidable engagement is substantially orthogonal to the direction of axial engagement, each engagement commonly engaging a set of electrical contacts disposed on said bottom surface of said illuminator.

27. An assembly as recited in claim 26, wherein one of said electrical devices is used to recharge said primary power source of said illuminator and the other of said electrical devices is used to at least one of supplement and replace said primary power source.

28. An assembly as recited in claim 27, wherein said illuminator includes means for preventing said primary power source from being charged while the light source is enabled.

29. An assembly as recited in claim 28, wherein said recharge preventing means includes a current charge limiting circuit disposed in said illuminator.

30. An assembly as recited in claim 27, wherein said primary power source is a rechargeable battery, said illuminator including means for converting power to said light source over a range of useful battery voltages between that of a fully charged battery and that of a nearly depleted battery.

31. An assembly as recited in claim 30, wherein said power conversion means includes a buck and boost circuit to maintain a substantially constant current to said light source over said range of useful battery voltages.

32. An assembly as recited in claim 26, including a flexible circuit assembly electrically interconnecting said light source and said primary power source, said flexible circuit assembly including at least one contact.

33. An assembly as recited in claim 32, wherein said at least one contact is integral to said flexible circuit assembly and extends from said electrical interface of said illuminator.

* * * * *